(12) United States Patent
Punt et al.

(10) Patent No.: US 9,290,772 B2
(45) Date of Patent: Mar. 22, 2016

(54) PRODUCTION OF ITACONIC ACID

(71) Applicant: NEDERLANDSE ORGANISATIE VOOR TOEGEPAST-NATUURWETENSCHAPPELIJK ONDERZOEK TNO, Delft (NL)

(72) Inventors: Peter Jan Punt, Houten (NL); Maria Johanna Van Der Werf, Tuil (NL)

(73) Assignee: DUTCH DNA BIOTECH B. V., Zeist (NL)

( * ) Notice: Subject to any disclaimer, the term of this patent is extended or adjusted under 35 U.S.C. 154(b) by 150 days.

(21) Appl. No.: 14/137,785

(22) Filed: Dec. 20, 2013

(65) Prior Publication Data

US 2014/0193885 A1    Jul. 10, 2014

Related U.S. Application Data

(62) Division of application No. 12/918,314, filed as application No. PCT/NL2009/050069 on Feb. 16, 2009, now Pat. No. 8,679,801.

(30) Foreign Application Priority Data

Feb. 18, 2008  (EP) .................... 08151584

(51) Int. Cl.
| | | |
|---|---|---|
| *C12N 1/20* | (2006.01) | |
| *C12P 7/44* | (2006.01) | |
| *C12P 7/46* | (2006.01) | |
| *C07H 21/04* | (2006.01) | |
| *C07K 14/00* | (2006.01) | |
| *C12N 15/80* | (2006.01) | |
| *C07K 14/38* | (2006.01) | |

(52) U.S. Cl.
CPC ............... *C12N 15/80* (2013.01); *C07K 14/38* (2013.01); *C12P 7/44* (2013.01)

(58) Field of Classification Search
None
See application file for complete search history.

(56) References Cited

U.S. PATENT DOCUMENTS 6,943,017 B2    9/2005    Hutchinson et al.
2004/0033570 A1    2/2004    Hutchinson et al.

OTHER PUBLICATIONS

Bonnarme et al., J. Bacteriol. (1995) 177(12):3573-3578.
Database UniProt [Online], Accession No. Q0C8L4, Oct. 17, 2006.
Dwiarti et al., J. Biosci. Bioeng. (2002) 94(1):29-33.
International Search Report for PCT/NL2009/050069, mailed on Jul. 6, 2009, 3 pages.
Jaklitsch et al., Journal of General Microbiology (1991) 137(3):533-540.
Kaplan et al., Journal of Biological Chemistry (19950 270(8):4108-4114.
Pel et al., "Genome sequencing and analysis of the versatile cell factory Aspergillus niger CBS 513.88," Nature Biotechnology (2007) 25:221-231, Epub Jan. 28, 2007.
Picault et al., Journal of biological Chemistry (2002) 277(27):24204-24211.

*Primary Examiner* — Iqbal H Chowdhury
(74) *Attorney, Agent, or Firm* — Morrison & Foerster LLP

(57) ABSTRACT

The invention relates to a nucleic acid sequence encoding an *Aspergillus* mitochondrial tricarboxylic acid transporter that can be used in the production of itaconic acid in microorganisms. Preferably said transporter protein is the protein encoded by the nucleic acid which is located on a chromosome segment of *A. terreus* that also harbors other genes involved in the itaconic acid biosynthesis and the lovastatin biosynthesis. Also, vectors, hosts and transformed microorganisms are part of the invention.

13 Claims, 5 Drawing Sheets

ATEG_09970 genomic sequence

ATGGACTCTAAAATCCAGACAAATGTTCCATTACCAAAGGCACCCCTTATCCAAAAAGCC
CGTGGAAGCGTGTATGTGTTCCTTCTTGGTCGCGCGTGGGCCATGTTACTGACAATCTC
TTTCTTAATATATGTACAGACGAAAGGCATTCCTGCAATGGTTGCGGGTGCTTGTGCTG
GGGCAGTTGAAATCTCCATCACCTACCCTTTCGAATGTGAGCTTTCCTGTGTTAAGAGT
TCTGCTTTACCGTGGCCGCCAACTGACAGTCTATTGCTTCGGCTGGTAGCGGCTAAAACT
CGCGCCCAGCTTAAGCGGCGAAACCATGATGTGGCAGCTATAAAACCTGGAATCCGAGGC
TGGTATGCTGGGTATGGAGCCACCTTGGTAGGAGCGAAAAGCCTCCGTTCGTATG
TAGCGATCCCCTTCATTCAAGCCAGCGTGGAGCTCGGCGTTTGCAATAACAAAC
AGAATTTGCCTCATTCAATATTTATCGCTGGCTTGGGTTGGGCTGACCGAGGCTGTCTTAGCCGT
AACTGGAGCTTCCGTCCTGGCTCAAGAGACAAAAATGTAAGTGCAAGATCTCACCCGTTATCCGA
ACCCCAGCGGAGGCGATCAAGAGACAAAAATGTAAGTGCAAGAAGGTTGGAAATGCAGAGTTAAG
CCAGTTCTTAATTCGTTCTCTTAGCATTGGGATCCTTCGAGATCGGGGACCGCTTGGATTCTTCTC
TGCCGGTTGGTCCTACAATTTGCGGCAGTCCCTCCAATGCCAGTGAAGTTCACTGTTTA
TAACGAACTTATTGGGCTGGCCGAAATACTGGAGTTTGCTGCCTGGTCGACACAGCCACT
GGCAAGCACCCTTGGTCGGTTCGGTTCTGTTACTGGAGTTTGCTGCCCTGGTCGACACAGCCACT
GGACCGTGATCAAGACACGGTAAGTAGTGCTCAGATGAATGCAATCTCTTCAGGCAAGACAACT
TATGCGTGACTTGGATGCGACTTCGGGTTACCTGCGTGAAAACACTCCTGCGCAGTGAAGGCATTGGCCTTTT
GTACGGAAATACCTTCAACTGCGTGAAAACACTCCTGCGCAGTGTATTCTTGTACACTGACAGACAACT
CTGGTCCGGTGTCTGGTTTCGGACAGGGAGACTTTCCCTTACCTCGGCCATCATGTTTCC
CGTGTAAGTTTAGGTAATCTACAGGCATGGTATTCTTGTACACTGACAGAGCGCCCAGC
TACGAGAAAGTCTACAAGTTCTTGACGCAACCAAACTGA

FIG. 3A

ATEG_09970 cDNA

ATGGACTCTAAAATCCAGACAAATGTTCCATTACCAAAGGCACCCCTTATCCAAAAGCC
CGTGGGAAGCGTACGAAAGGCATTCCTGCATTGGTTGCGGGTGCTTGCTGCTGGGCAGTT
GAAATCTCCATCACCTACCCTTTCGAATCGGCTAAAACTCGCGCCCAGCTTAAGCGGCGA
AACCATGATGTGGCAGCTATAAAAACCTGGAATCCGAGGCTGGTGCTCTGGGTATGGAGCC
ACCTTGGTAGGAACCACAGTGAAAGCCTCCGTTCAATTGCCTCATTCAATATTTATCGC
TCGGCCCTTTCGGGCCCAAATGGAGAGCTCTCAACTGGAGCTTCCGTCCTGGCTGGGTTT
GGGGCTGGCCGTGACCGAGGCTGTCTTAGCCGTAACCCCAGCGGAGGCGATCAAGACAAAA
ATCATTGATGCAAGGAAGGTTGGAAATGCAGAGTTAAGTACGACTTTTGGCGCGATAGCT
GGGATCCTTCGAGATCGGGACCGCTTGGATTCTCTGCGGTTGGTCCTACAATTTTG
CGGCAGTCCTCCAATGCGGCAGTGAAGTTCACTGTTTATAACGAACTTATTGGGCTGGCC
CGAAAATACTCGAAGAATGGCGAAGACGTGCACCCTCTGGCAAGCACTGATCAAGACACGAATG
GTTACTGGAGTTTGCTGCGCCTGGTCGACACAGCCACTGATCAAGACACGAATG
CAATCTCTTCAGGCAAGACAACTGTACGGAAATACCTTCAACTGCGTGAAAACACTCCTG
CGCAGTGAAGGCATTGGCGTTTCTGGTGTCTGGTTTCGGACAGGGAGACTTTCC
CTTACCTCGGCCATCATGTTTCCCGTCTACGAGAAAGTCTACAAGTTCTTGACGCAACCA
AACTGA

FIG. 3B

ATEG_09970 protein sequence

MDSKIQTNVPLPKAPLIQKAPLIQKARGKRTKGIPALVAGACAGAVEISITYPFESAKTRAQLKRR
NHDVAAIKPGIRGWYAGYGATLVGTTVKASVQFASFNIYRSALSGPNGELSTGASVLAGF
GAGVTEAVLAVTPAEAIKTKIIDARKVGNAELSTTFGAIAGILRDRGPLGFFSAVGPTIL
RQSSNAAVKFTVYNELIGLARKYSKNGEDVHPLASTLVGSVTGVCCAWSTQPLDVIKTRM
QSLQARQLYGNTFNCVKTLLRSEGIGVFWSGVWFRTGRLSLTSAIMFPVYEKVYKFLTQP
N*

FIG. 3C

SEQUENCE LISTING

<160> NUMBER OF SEQ ID NOS: 13

<210> SEQ ID NO 1
<211> LENGTH: 1299
<212> TYPE: DNA
<213> ORGANISM: Aspergillus terreus
<220> FEATURE:
<221> NAME/KEY: misc_feature
<222> LOCATION: (1)...(1299)
<223> OTHER INFORMATION: ATEG_0997.1 genomic sequence

<400> SEQUENCE: 1

```
atg gac tct aaa atc cag a caaatgttcc attaccaaag gcacccctta        49
tccaaaaagc ccgtgggaag cgtgtatgtg ttccttcttg gtcgcgcgtg ggccatgtta      109 ctgcaatct cttttcttaa tatatgtaca gacgaaaggc attcctgcat tggttgcggg      169
tgcttgtgct ggggcagttg aaatctccat cacctaccct ttcgaatgtg agctttcctg      229
tgtttaagag ttctgcttta ccgtggccgc caactgacag tctattgctt cggctggtag      289
cggctaaaac tcgcgcccag cttaagcggc gaaaccatga tgtggcagct ataaaacctg      349
gaatccgagg ctggtatgct gggtatggag ccaccttggt aggaaccaca gtgaaagcct      409
ccgttcgtat gtagcgatcc ccttctaagc cagcgtggag cgaaaaggaa tgaccgtttg      469
caataacaaa cagaatttgc ctcattcaat atttatcgct cggccctttc gggcccaaat      529
ggagagctct caactggagc ttccgtcctg gctgggtttg gggctggcgt gaccgaggct      589
gtcttagccg taacccccagc ggaggcgatc aagacaaaaa tgtaagttgc aacatctcac      649
ccgttatccg accagttctt aattcgttct cttagcattg atgcaaggaa ggttggaaat      709
gcagagttaa gtacgacttt tggcgcgata gctgggatcc ttcgagatcg gggaccgctt      769
ggattcttct ctgcggttgg tcctacaatt ttgcggcagt cctccaatgc ggcagtgaag      829
ttcactgttt ataacgaact tattgggctg gcccgaaaat actcgaagaa tggcgaagac      889
gtgcaccctc tggcaagcac cttggtcggt tctgttactg gagtttgctg cgcctggtcg      949
acacagccac tggacgtgat caagacacgg taagtagtgc tcagatcgac agtaacacgc      1009
```

-continued

| | |
|---|---|
| ccagataagt atatgctgac ttggatgcga cttcgggtta ccagaatgca atctcttcag | 1069 |
| gcaagacaac tgtacggaaa taccttcaac tgcgtgaaaa cactcctgcg cagtgaaggc | 1129 |
| attggcgttt tctggtccgg tgtctggttt cggacaggga gactttccct tacctcggcc | 1189 |
| atcatgtttc ccgtgtaagt ttagggtaat ctacaggcat ggtattcttg tacactgaca | 1249 |
| gagcgcccag ctacgagaaa gtctacaagt tcttgacgca accaaactga | 1299 |

```
<210> SEQ ID NO 2
<211> LENGTH: 906
<212> TYPE: DNA
<213> ORGANISM: Aspergillus terreus
<220> FEATURE:
<221> NAME/KEY: misc_feature
<222> LOCATION: (1)...(906)
<223> OTHER INFORMATION: ATEG_09970.1
<220> FEATURE:
<221> NAME/KEY: CDS
<222> LOCATION: (1)...(906)
```

<400> SEQUENCE: 2

| | | |
|---|---|---|
| atg gac tct aaa atc cag aca aat gtt cca tta cca aag gca ccc ctt<br>Met Asp Ser Lys Ile Gln Thr Asn Val Pro Leu Pro Lys Ala Pro Leu<br>1                5                10              15 | | 48 |
| atc caa aaa gcc cgt ggg aag cgt acg aaa ggc att cct gca ttg gtt<br>Ile Gln Lys Ala Arg Gly Lys Arg Thr Lys Gly Ile Pro Ala Leu Val<br>                20                25              30 | | 96 |
| gcg ggt gct tgt gct ggg gca gtt gaa atc tcc atc acc tac cct ttc<br>Ala Gly Ala Cys Ala Gly Ala Val Glu Ile Ser Ile Thr Tyr Pro Phe<br>            35                40              45 | | 144 |
| gaa tcg gct aaa act cgc gcc cag ctt aag cgg cga aac cat gat gtg<br>Glu Ser Ala Lys Thr Arg Ala Gln Leu Lys Arg Arg Asn His Asp Val<br>50                55                60 | | 192 |
| gca gct ata aaa cct gga atc cga ggc tgg tat gct ggg tat gga gcc<br>Ala Ala Ile Lys Pro Gly Ile Arg Gly Trp Tyr Ala Gly Tyr Gly Ala<br>65                70                75              80 | | 240 |
| acc ttg gta gga acc aca gtg aaa gcc tcc gtt caa ttt gcc tca ttc<br>Thr Leu Val Gly Thr Thr Val Lys Ala Ser Val Gln Phe Ala Ser Phe<br>            85                90              95 | | 288 |
| aat att tat cgc tcg gcc ctt tcg ggc cca aat gga gag ctc tca act<br>Asn Ile Tyr Arg Ser Ala Leu Ser Gly Pro Asn Gly Glu Leu Ser Thr<br>            100             105            110 | | 336 |
| gga gct tcc gtc ctg gct ggg ttt ggg gct ggc gtg acc gag gct gtc<br>Gly Ala Ser Val Leu Ala Gly Phe Gly Ala Gly Val Thr Glu Ala Val<br>            115             120            125 | | 384 |
| tta gcc gta acc cca gcg gag gcg atc aag aca aaa atc att gat gca<br>Leu Ala Val Thr Pro Ala Glu Ala Ile Lys Thr Lys Ile Ile Asp Ala<br>130               135            140 | | 432 |
| agg aag gtt gga aat gca gag tta agt acg act ttt ggc gcg ata gct<br>Arg Lys Val Gly Asn Ala Glu Leu Ser Thr Thr Phe Gly Ala Ile Ala<br>145               150            155              160 | | 480 |
| ggg atc ctt cga gat cgg gga ccg ctt gga ttc ttc tct gcg gtt ggt<br>Gly Ile Leu Arg Asp Arg Gly Pro Leu Gly Phe Phe Ser Ala Val Gly<br>            165             170            175 | | 528 |
| cct aca att ttg cgg cag tcc tcc aat gcg gca gtg aag ttc act gtt<br>Pro Thr Ile Leu Arg Gln Ser Ser Asn Ala Ala Val Lys Phe Thr Val<br>            180             185            190 | | 576 |
| tat aac gaa ctt att ggg ctg gcc cga aaa tac tcg aag aat ggc gaa<br>Tyr Asn Glu Leu Ile Gly Leu Ala Arg Lys Tyr Ser Lys Asn Gly Glu<br>            195             200            205 | | 624 |
| gac gtg cac cct ctg gca agc acc ttg gtc ggt tct gtt act gga gtt<br>Asp Val His Pro Leu Ala Ser Thr Leu Val Gly Ser Val Thr Gly Val | | 672 |

```
                   210                     215                     220
tgc tgc gcc tgg tcg aca cag cca ctg gac gtg atc aag aca cga atg       720
Cys Cys Ala Trp Ser Thr Gln Pro Leu Asp Val Ile Lys Thr Arg Met
225                 230                     235                 240 caa tct ctt cag gca aga caa ctg tac gga aat acc ttc aac tgc gtg       768
Gln Ser Leu Gln Ala Arg Gln Leu Tyr Gly Asn Thr Phe Asn Cys Val
                245                     250                     255 aaa aca ctc ctg cgc agt gaa ggc att ggc gtt ttc tgg tcc ggt gtc       816
Lys Thr Leu Leu Arg Ser Glu Gly Ile Gly Val Phe Trp Ser Gly Val
            260                     265                     270 tgg ttt cgg aca ggg aga ctt tcc ctt acc tcg gcc atc atg ttt ccc       864
Trp Phe Arg Thr Gly Arg Leu Ser Leu Thr Ser Ala Ile Met Phe Pro
        275                     280                     285 gtc tac gag aaa gtc tac aag ttc ttg acg caa cca aac tga               906
Val Tyr Glu Lys Val Tyr Lys Phe Leu Thr Gln Pro Asn
    290                     295                     300
```

<210> SEQ ID NO 3
<211> LENGTH: 301
<212> TYPE: PRT
<213> ORGANISM: Aspergillus terreus
<220> FEATURE:
<221> NAME/KEY: misc_feature
<222> LOCATION: (1)...(301)
<223> OTHER INFORMATION: translation of ATEG_09970.1

<400> SEQUENCE: 3

```
Met Asp Ser Lys Ile Gln Thr Asn Val Pro Leu Pro Lys Ala Pro Leu
 1               5                  10                  15

Ile Gln Lys Ala Arg Gly Lys Arg Thr Lys Gly Ile Pro Ala Leu Val
                20                  25                  30

Ala Gly Ala Cys Ala Gly Ala Val Glu Ile Ser Ile Thr Tyr Pro Phe
            35                  40                  45

Glu Ser Ala Lys Thr Arg Ala Gln Leu Lys Arg Arg Asn His Asp Val
        50                  55                  60

Ala Ala Ile Lys Pro Gly Ile Arg Gly Trp Tyr Ala Gly Tyr Gly Ala
65                  70                  75                  80

Thr Leu Val Gly Thr Thr Val Lys Ala Ser Val Gln Phe Ala Ser Phe
                85                  90                  95

Asn Ile Tyr Arg Ser Ala Leu Ser Gly Pro Asn Gly Glu Leu Ser Thr
            100                 105                 110

Gly Ala Ser Val Leu Ala Gly Phe Gly Ala Gly Val Thr Glu Ala Val
        115                 120                 125

Leu Ala Val Thr Pro Ala Glu Ala Ile Lys Thr Lys Ile Ile Asp Ala
    130                 135                 140

Arg Lys Val Gly Asn Ala Glu Leu Ser Thr Thr Phe Gly Ala Ile Ala
145                 150                 155                 160

Gly Ile Leu Arg Asp Arg Gly Pro Leu Gly Phe Phe Ser Ala Val Gly
                165                 170                 175

Pro Thr Ile Leu Arg Gln Ser Ser Asn Ala Ala Val Lys Phe Thr Val
            180                 185                 190

Tyr Asn Glu Leu Ile Gly Leu Ala Arg Lys Tyr Ser Lys Asn Gly Glu
        195                 200                 205

Asp Val His Pro Leu Ala Ser Thr Leu Val Gly Ser Val Thr Gly Val
    210                 215                 220

Cys Cys Ala Trp Ser Thr Gln Pro Leu Asp Val Ile Lys Thr Arg Met
225                 230                 235                 240
```

```
                    Gln Ser Leu Gln Ala Arg Gln Leu Tyr Gly Asn Thr Phe Asn Cys Val
                                    245                 250                 255

Lys Thr Leu Leu Arg Ser Glu Gly Ile Gly Val Phe Trp Ser Gly Val
                                260                 265                 270

Trp Phe Arg Thr Gly Arg Leu Ser Leu Thr Ser Ala Ile Met Phe Pro
                            275                 280                 285

Val Tyr Glu Lys Val Tyr Lys Phe Leu Thr Gln Pro Asn
                        290                 295                 300

<210> SEQ ID NO 4
<211> LENGTH: 1473
<212> TYPE: DNA
<213> ORGANISM: Aspergillus terreus
<220> FEATURE:
<221> NAME/KEY: misc_feature
<222> LOCATION: (1)...(1473)
<223> OTHER INFORMATION: ATEG_09971.1
<220> FEATURE:
<221> NAME/KEY: CDS
<222> LOCATION: (1)...(1473)

<400> SEQUENCE: 4
```

| atg acc aag caa tct gcg gac agc aac gca aag tca gga gtt acg gcc | 48 |
|---|---|
| Met Thr Lys Gln Ser Ala Asp Ser Asn Ala Lys Ser Gly Val Thr Ala | |
| 1               5                   10                  15 | |

| gaa ata tgc cat tgg gca tcc aac ctg gcc act gac gac atc cct tcg | 96 |
|---|---|
| Glu Ile Cys His Trp Ala Ser Asn Leu Ala Thr Asp Asp Ile Pro Ser | |
|                 20                  25                  30 | |

| gac gta tta gaa aga gcg aaa tac ctg att ctc gat ggt att gca tgt | 144 |
|---|---|
| Asp Val Leu Glu Arg Ala Lys Tyr Leu Ile Leu Asp Gly Ile Ala Cys | |
|         35                  40                  45 | |

| gcc tgg gtt ggt gca aga gtg cct tgg tca gag aag tat gtg cag gca | 192 |
|---|---|
| Ala Trp Val Gly Ala Arg Val Pro Trp Ser Glu Lys Tyr Val Gln Ala | |
|     50                  55                  60 | |

| aca atg agc ttt gag ccg cca gga gcc tgc agg gtg att gga tat ggg | 240 |
|---|---|
| Thr Met Ser Phe Glu Pro Pro Gly Ala Cys Arg Val Ile Gly Tyr Gly | |
| 65                  70                  75                  80 | |

| cag aaa ctg ggg cct gtt gca gca gcc atg acc aat tcc gct ttc ata | 288 |
|---|---|
| Gln Lys Leu Gly Pro Val Ala Ala Ala Met Thr Asn Ser Ala Phe Ile | |
|                 85                  90                  95 | |

| cag gcc aca gag ctt gac gac tac cac agc gaa gcc ccc cta cac tct | 336 |
|---|---|
| Gln Ala Thr Glu Leu Asp Asp Tyr His Ser Glu Ala Pro Leu His Ser | |
|             100                 105                 110 | |

| gca agc atc gtc ctc cct gcg gtc ttt gca gca agt gag gtc tta gcc | 384 |
|---|---|
| Ala Ser Ile Val Leu Pro Ala Val Phe Ala Ala Ser Glu Val Leu Ala | |
|         115                 120                 125 | |

| gag caa ggc aaa aca att tct ggt ata gat gtc att cta gcc gcc att | 432 |
|---|---|
| Glu Gln Gly Lys Thr Ile Ser Gly Ile Asp Val Ile Leu Ala Ala Ile | |
|     130                 135                 140 | |

| gtg ggg ttt gaa tct ggc ccg cgg atc ggc aaa gca att tac gga tcg | 480 |
|---|---|
| Val Gly Phe Glu Ser Gly Pro Arg Ile Gly Lys Ala Ile Tyr Gly Ser | |
| 145                 150                 155                 160 | |

| gac ctc ttg aac aac ggc tgg cat tgt gga gcc gtg tat ggt gct cca | 528 |
|---|---|
| Asp Leu Leu Asn Asn Gly Trp His Cys Gly Ala Val Tyr Gly Ala Pro | |
|                 165                 170                 175 | |

| gct ggt gcg ctg gcc aca gga aag ctc ctc ggt cta act cca gac tcc | 576 |
|---|---|
| Ala Gly Ala Leu Ala Thr Gly Lys Leu Leu Gly Leu Thr Pro Asp Ser | |
|             180                 185                 190 | |

| atg gaa gat gct ctc gga atc gcg tgc acg caa gcc tgt ggt tta atg | 624 |
|---|---|
| Met Glu Asp Ala Leu Gly Ile Ala Cys Thr Gln Ala Cys Gly Leu Met | |
|         195                 200                 205 | |

```
tcg gcg caa tac gga ggc atg gtc aag cgc gtg caa cat gga ttc gca    672
Ser Ala Gln Tyr Gly Gly Met Val Lys Arg Val Gln His Gly Phe Ala
210                 215                 220 gcg cgt aat ggt ctt ctt ggg gga ctg ttg gcc tat ggt ggg tac gag    720
Ala Arg Asn Gly Leu Leu Gly Gly Leu Leu Ala Tyr Gly Gly Tyr Glu
225                 230                 235                 240 gcc atg aag ggt gtc ctg gag aga tct tat ggc ggt ttc ctc aaa atg    768
Ala Met Lys Gly Val Leu Glu Arg Ser Tyr Gly Gly Phe Leu Lys Met
                245                 250                 255 ttc acc aag ggc aat ggc aga gag cct ccc tac aaa gag gag gaa gtg    816
Phe Thr Lys Gly Asn Gly Arg Glu Pro Pro Tyr Lys Glu Glu Glu Val
            260                 265                 270 gtg gcc ggt ctc ggt tca ttc tgg cat acc ttt act att cgc atc aag    864
Val Ala Gly Leu Gly Ser Phe Trp His Thr Phe Thr Ile Arg Ile Lys
        275                 280                 285 ctc tat gcc tgc tgc gga ctt gtc cat ggt cca gtc gaa gct atc gaa    912
Leu Tyr Ala Cys Cys Gly Leu Val His Gly Pro Val Glu Ala Ile Glu
    290                 295                 300 aag ctt cag agg aga tac ccc gag ctc ttg aat aga gcc aac ctc agc    960
Lys Leu Gln Arg Arg Tyr Pro Glu Leu Leu Asn Arg Ala Asn Leu Ser
305                 310                 315                 320 aac att cgc cat gtt tat gta cag ctt tca aca gcc tcg aac agt cac   1008
Asn Ile Arg His Val Tyr Val Gln Leu Ser Thr Ala Ser Asn Ser His
                325                 330                 335 tgt gga tgg ata cca gag gag agg ccc atc agt tca atc gca ggg cag   1056
Cys Gly Trp Ile Pro Glu Glu Arg Pro Ile Ser Ser Ile Ala Gly Gln
            340                 345                 350 atg agt gtc gca tac atc ctc gcc gtc cag ctg gtc gac cag caa tgt   1104
Met Ser Val Ala Tyr Ile Leu Ala Val Gln Leu Val Asp Gln Gln Cys
        355                 360                 365 ctt ctg gct cag ttt tct gag ttt gat gac aac ttg gag aga cca gaa   1152
Leu Leu Ala Gln Phe Ser Glu Phe Asp Asp Asn Leu Glu Arg Pro Glu
    370                 375                 380 gtg tgg gat ctg gcc agg aag gtt act cca tct cat agc gaa gag ttt   1200
Val Trp Asp Leu Ala Arg Lys Val Thr Pro Ser His Ser Glu Glu Phe
385                 390                 395                 400 gat caa gac ggc aac tgt ctc agt gcg ggt cgc gtg agg att gag ttc   1248
Asp Gln Asp Gly Asn Cys Leu Ser Ala Gly Arg Val Arg Ile Glu Phe
                405                 410                 415 aac gat ggc tct tct gtt acg gaa act gtc gag aag cct ctt gga gtc   1296
Asn Asp Gly Ser Ser Val Thr Glu Thr Val Glu Lys Pro Leu Gly Val
            420                 425                 430 aaa gag ccc atg cca aac gaa cgg att ctc cac aaa tac cga acc ctt   1344
Lys Glu Pro Met Pro Asn Glu Arg Ile Leu His Lys Tyr Arg Thr Leu
        435                 440                 445 gcg ggt agc gtg acg gac gaa tcc cgg gtg aaa gag att gag gat ctt   1392
Ala Gly Ser Val Thr Asp Glu Ser Arg Val Lys Glu Ile Glu Asp Leu
    450                 455                 460 gtc ctc agc ctg gac agg ctc acc gac att acc cca ttg ctg gag ctg   1440
Val Leu Ser Leu Asp Arg Leu Thr Asp Ile Thr Pro Leu Leu Glu Leu
465                 470                 475                 480 ctt aat tgt ccc gtg aaa tcg cca ctg gta taa                       1473
Leu Asn Cys Pro Val Lys Ser Pro Leu Val
                485                 490
```

<210> SEQ ID NO 5
<211> LENGTH: 490
<212> TYPE: PRT
<213> ORGANISM: Aspergillus terreus
<220> FEATURE:
<221> NAME/KEY: misc_feature
<222> LOCATION: (1)...(490)
<223> OTHER INFORMATION: translation of ATEG_09971.1

<400> SEQUENCE: 5

```
Met Thr Lys Gln Ser Ala Asp Ser Asn Ala Lys Ser Gly Val Thr Ala
 1               5                  10                  15

Glu Ile Cys His Trp Ala Ser Asn Leu Ala Thr Asp Asp Ile Pro Ser
             20                  25                  30

Asp Val Leu Glu Arg Ala Lys Tyr Leu Ile Leu Asp Gly Ile Ala Cys
         35                  40                  45

Ala Trp Val Gly Ala Arg Val Pro Trp Ser Glu Lys Tyr Val Gln Ala
     50                  55                  60

Thr Met Ser Phe Glu Pro Pro Gly Ala Cys Arg Val Ile Gly Tyr Gly
 65                 70                  75                  80

Gln Lys Leu Gly Pro Val Ala Ala Ala Met Thr Asn Ser Ala Phe Ile
             85                  90                  95

Gln Ala Thr Glu Leu Asp Asp Tyr His Ser Glu Ala Pro Leu His Ser
        100                 105                 110

Ala Ser Ile Val Leu Pro Ala Val Phe Ala Ala Ser Glu Val Leu Ala
    115                 120                 125

Glu Gln Gly Lys Thr Ile Ser Gly Ile Asp Val Ile Leu Ala Ala Ile
130                 135                 140

Val Gly Phe Glu Ser Gly Pro Arg Ile Gly Lys Ala Ile Tyr Gly Ser
145                 150                 155                 160

Asp Leu Leu Asn Asn Gly Trp His Cys Gly Ala Val Tyr Gly Ala Pro
                165                 170                 175

Ala Gly Ala Leu Ala Thr Gly Lys Leu Leu Gly Leu Thr Pro Asp Ser
            180                 185                 190

Met Glu Asp Ala Leu Gly Ile Ala Cys Thr Gln Ala Cys Gly Leu Met
        195                 200                 205

Ser Ala Gln Tyr Gly Gly Met Val Lys Arg Val Gln His Gly Phe Ala
    210                 215                 220

Ala Arg Asn Gly Leu Leu Gly Gly Leu Leu Ala Tyr Gly Gly Tyr Glu
225                 230                 235                 240

Ala Met Lys Gly Val Leu Glu Arg Ser Tyr Gly Gly Phe Leu Lys Met
                245                 250                 255

Phe Thr Lys Gly Asn Gly Arg Glu Pro Pro Tyr Lys Glu Glu Glu Val
            260                 265                 270

Val Ala Gly Leu Gly Ser Phe Trp His Thr Phe Thr Ile Arg Ile Lys
        275                 280                 285

Leu Tyr Ala Cys Cys Gly Leu Val His Gly Pro Val Glu Ala Ile Glu
    290                 295                 300

Lys Leu Gln Arg Arg Tyr Pro Glu Leu Leu Asn Arg Ala Asn Leu Ser
305                 310                 315                 320

Asn Ile Arg His Val Tyr Val Gln Leu Ser Thr Ala Ser Asn Ser His
                325                 330                 335

Cys Gly Trp Ile Pro Glu Glu Arg Pro Ile Ser Ser Ile Ala Gly Gln
            340                 345                 350

Met Ser Val Ala Tyr Ile Leu Ala Val Gln Leu Val Asp Gln Gln Cys
        355                 360                 365

Leu Leu Ala Gln Phe Ser Glu Phe Asp Asp Asn Leu Glu Arg Pro Glu
    370                 375                 380

Val Trp Asp Leu Ala Arg Lys Val Thr Pro Ser His Ser Glu Glu Phe
385                 390                 395                 400
```

Asp Gln Asp Gly Asn Cys Leu Ser Ala Gly Arg Val Arg Ile Glu Phe
                405                 410                 415

Asn Asp Gly Ser Ser Val Thr Glu Thr Val Glu Lys Pro Leu Gly Val
            420                 425                 430

Lys Glu Pro Met Pro Asn Glu Arg Ile Leu His Lys Tyr Arg Thr Leu
        435                 440                 445

Ala Gly Ser Val Thr Asp Glu Ser Arg Val Lys Glu Ile Glu Asp Leu
    450                 455                 460

Val Leu Ser Leu Asp Arg Leu Thr Asp Ile Thr Pro Leu Leu Glu Leu
465                 470                 475                 480

Leu Asn Cys Pro Val Lys Ser Pro Leu Val
                485                 490

<210> SEQ ID NO 6
<211> LENGTH: 22
<212> TYPE: DNA
<213> ORGANISM: Artificial Sequence
<220> FEATURE:
<223> OTHER INFORMATION: primer

<400> SEQUENCE: 6
atcgtcatga ccaagcaatc tg                                              22

<210> SEQ ID NO 7
<211> LENGTH: 28
<212> TYPE: DNA
<213> ORGANISM: Artificial Sequence
<220> FEATURE:
<223> OTHER INFORMATION: primer

<400> SEQUENCE: 7
atcgtcatga ccaagcaatc tgcggaca                                        28

<210> SEQ ID NO 8
<211> LENGTH: 28
<212> TYPE: DNA
<213> ORGANISM: Artificial Sequence
<220> FEATURE:
<223> OTHER INFORMATION: reverse primer

<400> SEQUENCE: 8
tttagcggtg accatattcc taggccct                                        28

<210> SEQ ID NO 9
<211> LENGTH: 33
<212> TYPE: DNA
<213> ORGANISM: Artificial Sequence
<220> FEATURE:
<223> OTHER INFORMATION: reverse primer

<400> SEQUENCE: 9
ggcattttag cggtgaccat attcctaggc ccc                                  33

<210> SEQ ID NO 10
<211> LENGTH: 861
<212> TYPE: DNA
<213> ORGANISM: Aspergillus niger
<220> FEATURE:
<221> NAME/KEY: misc_feature
<222> LOCATION: (1)...(861)
<223> OTHER INFORMATION: ATEG_09970.1
<220> FEATURE:
<221> NAME/KEY: CDS
<222> LOCATION: (1)...(861)

```
<400> SEQUENCE: 10 atg agt att caa cat ttc cgt gtc gcc ctt att ccc ttt ttt gcg gca      48
Met Ser Ile Gln His Phe Arg Val Ala Leu Ile Pro Phe Phe Ala Ala
1               5                   10                  15 ttt tgc ctt cct gtt ttt gct cac cca gaa acg ctg gtg aaa gta aaa      96
Phe Cys Leu Pro Val Phe Ala His Pro Glu Thr Leu Val Lys Val Lys
            20                  25                  30 gat gct gaa gat cag ttg ggt gca cga gtg ggt tac atc gaa ctg gat     144
Asp Ala Glu Asp Gln Leu Gly Ala Arg Val Gly Tyr Ile Glu Leu Asp
        35                  40                  45 ctc aac agc ggt aag atc ctt gag agt ttt cgc ccc gaa gaa cgt ttt     192
Leu Asn Ser Gly Lys Ile Leu Glu Ser Phe Arg Pro Glu Glu Arg Phe
    50                  55                  60 cca atg atg agc act ttt aaa gtt ctg cta tgt ggc gcg gta tta tcc     240
Pro Met Met Ser Thr Phe Lys Val Leu Leu Cys Gly Ala Val Leu Ser
65                  70                  75                  80 cgt att gac gcc ggg caa gag caa ctc ggt cgc cgc ata cac tat tct     288
Arg Ile Asp Ala Gly Gln Glu Gln Leu Gly Arg Arg Ile His Tyr Ser
                85                  90                  95 cag aat gac ttg gtt gag tac tca cca gtc aca gaa aag cat ctt acg     336
Gln Asn Asp Leu Val Glu Tyr Ser Pro Val Thr Glu Lys His Leu Thr
            100                 105                 110 gat ggc atg aca gta aga gaa tta tgc agt gct gcc ata acc atg agt     384
Asp Gly Met Thr Val Arg Glu Leu Cys Ser Ala Ala Ile Thr Met Ser
        115                 120                 125 gat aac act gcg gcc aac tta ctt ctg aca acg atc gga gga ccg aag     432
Asp Asn Thr Ala Ala Asn Leu Leu Leu Thr Thr Ile Gly Gly Pro Lys
    130                 135                 140 gag cta acc gct ttt ttg cac aac atg ggg gat cat gta act cgc ctt     480
Glu Leu Thr Ala Phe Leu His Asn Met Gly Asp His Val Thr Arg Leu
145                 150                 155                 160 gat cgt tgg gaa ccg gag ctg aat gaa gcc ata cca aac gac gag cgt     528
Asp Arg Trp Glu Pro Glu Leu Asn Glu Ala Ile Pro Asn Asp Glu Arg
                165                 170                 175 gac acc acg atg cct gta gca atg gca aca acg ttg cgc aaa cta tta     576
Asp Thr Thr Met Pro Val Ala Met Ala Thr Thr Leu Arg Lys Leu Leu
            180                 185                 190 act ggc gaa cta ctt act cta gct tcc cgg caa caa tta ata gac tgg     624
Thr Gly Glu Leu Leu Thr Leu Ala Ser Arg Gln Gln Leu Ile Asp Trp
        195                 200                 205 atg gag gcg gat aaa gtt gca gga cca ctt ctg cgc tcg gcc ctt ccg     672
Met Glu Ala Asp Lys Val Ala Gly Pro Leu Leu Arg Ser Ala Leu Pro
    210                 215                 220 gct ggc tgg ttt att gct gat aaa tct gga gcc ggt gag cgt ggg tct     720
Ala Gly Trp Phe Ile Ala Asp Lys Ser Gly Ala Gly Glu Arg Gly Ser
225                 230                 235                 240 cgc ggt atc att gca gca ctg ggg cca gat ggt aag ccc tcc cgt atc     768
Arg Gly Ile Ile Ala Ala Leu Gly Pro Asp Gly Lys Pro Ser Arg Ile
                245                 250                 255 gta gtt atc tac acg acg ggg agt cag gca act atg gat gaa cga aat     816
Val Val Ile Tyr Thr Thr Gly Ser Gln Ala Thr Met Asp Glu Arg Asn
            260                 265                 270 aga cag atc gct gag ata ggt gcc tca ctg att aag cat tgg taa         861
Arg Gln Ile Ala Glu Ile Gly Ala Ser Leu Ile Lys His Trp
        275                 280                 285

<210> SEQ ID NO 11
<211> LENGTH: 286
<212> TYPE: PRT
```

<213> ORGANISM: Aspergillus niger
<220> FEATURE:
<221> NAME/KEY: misc_feature
<222> LOCATION: (1)...(286)
<223> OTHER INFORMATION: translation of ATEG_09970.1

<400> SEQUENCE: 11

```
Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Asp Gln Leu Gly Ala Arg Val Gly Tyr Ile Glu Leu Asp
        35                  40                  45

Leu Asn Ser Gly Lys Ile Leu Glu Ser Phe Arg Pro Glu Glu Arg Phe
50                  55                  60

Pro Met Met Ser Thr Phe Lys Val Leu Leu Cys Gly Ala Val Leu Ser
65                  70                  75                  80

Arg Ile Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
        275                 280                 285
```

<210> SEQ ID NO 12
<211> LENGTH: 1212
<212> TYPE: DNA
<213> ORGANISM: Aspergillus terreus
<220> FEATURE:
<221> NAME/KEY: misc_feature
<222> LOCATION: (1)...(1212)
<223> OTHER INFORMATION: ATEG_09972.1
<220> FEATURE:
<221> NAME/KEY: CDS
<222> LOCATION: (1)...(1212)

<400> SEQUENCE: 12

```
atg ggc cac ggt gac act gag tcc ccg aac cca acg acg acc acg gaa      48
Met Gly His Gly Asp Thr Glu Ser Pro Asn Pro Thr Thr Thr Thr Glu
```

| | | | | | | | | | | | | | | | | |
|---|---|---|---|---|---|---|---|---|---|---|---|---|---|---|---|---|
| 1 | | | | 5 | | | | | 10 | | | | | 15 | | |

```
ggt  agc  gga  caa  aac  gag  cca  gag  aaa  aag  ggc  cgt  gat  att  cca  tta          96
Gly  Ser  Gly  Gln  Asn  Glu  Pro  Glu  Lys  Lys  Gly  Arg  Asp  Ile  Pro  Leu
                   20                      25                      30 tgg  aga  aaa  tgt  gtc  att  acg  ttt  gtt  gtt  agt  tgg  atg  act  cta  gtc         144
Trp  Arg  Lys  Cys  Val  Ile  Thr  Phe  Val  Val  Ser  Trp  Met  Thr  Leu  Val
          35                      40                      45 gtt  act  ttc  tcc  agt  act  tgt  ctt  ctt  cct  gcc  gcc  cct  gaa  atc  gcg         192
Val  Thr  Phe  Ser  Ser  Thr  Cys  Leu  Leu  Pro  Ala  Ala  Pro  Glu  Ile  Ala
     50                      55                      60 aat  gaa  ttt  gat  atg  act  gtc  gag  act  atc  aac  atc  tcc  aat  gct  ggt         240
Asn  Glu  Phe  Asp  Met  Thr  Val  Glu  Thr  Ile  Asn  Ile  Ser  Asn  Ala  Gly
65                      70                      75                      80 gtc  cta  gtt  gcc  atg  gga  tat  tca  tcc  ctc  ata  tgg  ggt  ccc  atg  aac         288
Val  Leu  Val  Ala  Met  Gly  Tyr  Ser  Ser  Leu  Ile  Trp  Gly  Pro  Met  Asn
                    85                      90                      95 aag  tta  gtc  ggc  cgg  cgg  aca  tca  tac  aat  ctg  gcc  att  tca  atg  ctt         336
Lys  Leu  Val  Gly  Arg  Arg  Thr  Ser  Tyr  Asn  Leu  Ala  Ile  Ser  Met  Leu
               100                     105                     110 tgt  gca  tgc  tcc  gct  gga  acg  gca  gcg  gcg  ata  aac  gag  gaa  atg  ttc         384
Cys  Ala  Cys  Ser  Ala  Gly  Thr  Ala  Ala  Ala  Ile  Asn  Glu  Glu  Met  Phe
          115                     120                     125 ata  gcg  ttc  aga  gtg  ttg  agc  ggc  tta  acc  gga  acc  tcg  ttc  atg  gtc         432
Ile  Ala  Phe  Arg  Val  Leu  Ser  Gly  Leu  Thr  Gly  Thr  Ser  Phe  Met  Val
     130                     135                     140 tca  ggc  caa  act  gtt  ctt  gca  gat  atc  ttt  gag  cct  gtt  tac  cgt  ggg         480
Ser  Gly  Gln  Thr  Val  Leu  Ala  Asp  Ile  Phe  Glu  Pro  Val  Tyr  Arg  Gly
145                     150                     155                     160 acg  gcc  gta  ggt  ttc  ttc  atg  gcc  ggg  act  ctt  tct  ggc  cct  gca  ata         528
Thr  Ala  Val  Gly  Phe  Phe  Met  Ala  Gly  Thr  Leu  Ser  Gly  Pro  Ala  Ile
                    165                     170                     175 ggc  ccc  tgc  gtg  gga  ggg  gtc  atc  gtc  act  ttc  acg  agt  tgg  cgt  gtt         576
Gly  Pro  Cys  Val  Gly  Gly  Val  Ile  Val  Thr  Phe  Thr  Ser  Trp  Arg  Val
               180                     185                     190 atc  ttc  tgg  ctt  caa  cta  ggt  atg  agc  ggg  ctg  ggg  ctc  gtg  ctt  tct         624
Ile  Phe  Trp  Leu  Gln  Leu  Gly  Met  Ser  Gly  Leu  Gly  Leu  Val  Leu  Ser
          195                     200                     205 ctg  cta  ttt  ttc  ccg  aaa  atc  gaa  gga  aat  tct  gag  aag  gtc  tca  acg         672
Leu  Leu  Phe  Phe  Pro  Lys  Ile  Glu  Gly  Asn  Ser  Glu  Lys  Val  Ser  Thr
     210                     215                     220 gcg  ttt  aaa  ccg  acc  aca  ctt  gtc  aca  atc  ata  tcg  aaa  ttc  tcc  cca         720
Ala  Phe  Lys  Pro  Thr  Thr  Leu  Val  Thr  Ile  Ile  Ser  Lys  Phe  Ser  Pro
225                     230                     235                     240 acg  gat  gtg  ctc  aag  cag  tgg  gtg  tat  cca  aat  gtc  ttt  ctt  gcc  gac         768
Thr  Asp  Val  Leu  Lys  Gln  Trp  Val  Tyr  Pro  Asn  Val  Phe  Leu  Ala  Asp
                    245                     250                     255 tta  tgc  tgt  ggc  ctc  ctg  gca  atc  acg  caa  tat  tcg  atc  ctg  act  tca         816
Leu  Cys  Cys  Gly  Leu  Leu  Ala  Ile  Thr  Gln  Tyr  Ser  Ile  Leu  Thr  Ser
               260                     265                     270 gct  cgt  gcc  ata  ttc  aac  tca  cga  ttt  cat  tta  acg  act  gcc  cta  gta         864
Ala  Arg  Ala  Ile  Phe  Asn  Ser  Arg  Phe  His  Leu  Thr  Thr  Ala  Leu  Val
          275                     280                     285 tcg  ggt  ctc  ttc  tac  ctc  gct  cca  ggt  gcc  ggg  ttc  ctg  ata  ggc  agt         912
Ser  Gly  Leu  Phe  Tyr  Leu  Ala  Pro  Gly  Ala  Gly  Phe  Leu  Ile  Gly  Ser
     290                     295                     300 ctc  gtc  ggc  ggt  aaa  ctt  tcg  gat  cgc  acc  gtt  cgg  aga  tac  ata  gta         960
Leu  Val  Gly  Gly  Lys  Leu  Ser  Asp  Arg  Thr  Val  Arg  Arg  Tyr  Ile  Val
305                     310                     315                     320 aag  cgc  gga  ttc  cgt  ctc  cct  cag  gat  cga  ctc  cac  agc  ggg  ctc  atc        1008
```

```
                Lys Arg Gly Phe Arg Leu Pro Gln Asp Arg Leu His Ser Gly Leu Ile
                                325                 330                 335 aca ttg ttc gcc gtg ctg ccc gca gga acg ctc att tac ggg tgg aca           1056
Thr Leu Phe Ala Val Leu Pro Ala Gly Thr Leu Ile Tyr Gly Trp Thr
            340                 345                 350 ctc caa gag gat aag ggt gat atg gta gtg ccc ata atc gcg gcg ttc           1104
Leu Gln Glu Asp Lys Gly Asp Met Val Val Pro Ile Ile Ala Ala Phe
        355                 360                 365 ttc gcg ggc tgg ggg ctc atg ggc agt ttt aac tgc ctg aac act tac           1152
Phe Ala Gly Trp Gly Leu Met Gly Ser Phe Asn Cys Leu Asn Thr Tyr
    370                 375                 380 gtg gct ggt ttg ttc cac acc ctc att tat cta ttc cct ttg tgt aca           1200
Val Ala Gly Leu Phe His Thr Leu Ile Tyr Leu Phe Pro Leu Cys Thr
385                 390                 395                 400 tgc cca caa taa                                                           1212
Cys Pro Gln <210> SEQ ID NO 13
<211> LENGTH: 403
<212> TYPE: PRT
<213> ORGANISM: Aspergillus terreus
<220> FEATURE:
<221> NAME/KEY: misc_feature
<222> LOCATION: (1)...(403)
<223> OTHER INFORMATION: translation of ATEG_09972.1

<400> SEQUENCE: 13

Met Gly His Gly Asp Thr Glu Ser Pro Asn Pro Thr Thr Thr Thr Glu
 1               5                  10                  15

Gly Ser Gly Gln Asn Glu Pro Glu Lys Lys Gly Arg Asp Ile Pro Leu
            20                  25                  30

Trp Arg Lys Cys Val Ile Thr Phe Val Val Ser Trp Met Thr Leu Val
        35                  40                  45

Val Thr Phe Ser Ser Thr Cys Leu Leu Pro Ala Ala Pro Glu Ile Ala
    50                  55                  60

Asn Glu Phe Asp Met Thr Val Glu Thr Ile Asn Ile Ser Asn Ala Gly
65                  70                  75                  80

Val Leu Val Ala Met Gly Tyr Ser Ser Leu Ile Trp Gly Pro Met Asn
                85                  90                  95

Lys Leu Val Gly Arg Arg Thr Ser Tyr Asn Leu Ala Ile Ser Met Leu
            100                 105                 110

Cys Ala Cys Ser Ala Gly Thr Ala Ala Ala Ile Asn Glu Glu Met Phe
        115                 120                 125

Ile Ala Phe Arg Val Leu Ser Gly Leu Thr Gly Thr Ser Phe Met Val
    130                 135                 140

Ser Gly Gln Thr Val Leu Ala Asp Ile Phe Glu Pro Val Tyr Arg Gly
145                 150                 155                 160

Thr Ala Val Gly Phe Phe Met Ala Gly Thr Leu Ser Gly Pro Ala Ile
                165                 170                 175

Gly Pro Cys Val Gly Gly Val Ile Val Thr Phe Thr Ser Trp Arg Val
            180                 185                 190

Ile Phe Trp Leu Gln Leu Gly Met Ser Gly Leu Gly Leu Val Leu Ser
        195                 200                 205

Leu Leu Phe Phe Pro Lys Ile Glu Gly Asn Ser Glu Lys Val Ser Thr
    210                 215                 220

Ala Phe Lys Pro Thr Thr Leu Val Thr Ile Ile Ser Lys Phe Ser Pro
225                 230                 235                 240
```

-continued

```
Thr Asp Val Leu Lys Gln Trp Val Tyr Pro Asn Val Phe Leu Ala Asp
                245                 250                 255
Leu Cys Cys Gly Leu Leu Ala Ile Thr Gln Tyr Ser Ile Leu Thr Ser
            260                 265                 270
Ala Arg Ala Ile Phe Asn Ser Arg Phe His Leu Thr Thr Ala Leu Val
            275                 280                 285
Ser Gly Leu Phe Tyr Leu Ala Pro Gly Ala Gly Phe Leu Ile Gly Ser
        290                 295                 300
Leu Val Gly Gly Lys Leu Ser Asp Arg Thr Val Arg Arg Tyr Ile Val
305                 310                 315                 320
Lys Arg Gly Phe Arg Leu Pro Gln Asp Arg Leu His Ser Gly Leu Ile
                325                 330                 335
Thr Leu Phe Ala Val Leu Pro Ala Gly Thr Leu Ile Tyr Gly Trp Thr
                340                 345                 350
Leu Gln Glu Asp Lys Gly Asp Met Val Val Pro Ile Ile Ala Ala Phe
            355                 360                 365
Phe Ala Gly Trp Gly Leu Met Gly Ser Phe Asn Cys Leu Asn Thr Tyr
        370                 375                 380
Val Ala Gly Leu Phe His Thr Leu Ile Tyr Leu Phe Pro Leu Cys Thr
385                 390                 395                 400
Cys Pro Gln
```

PRODUCTION OF ITACONIC ACID

CROSS REFERENCE TO RELATED APPLICATIONS

This application is a divisional of copending U.S. Ser. No. 12/918,314 having an international filing date of 16 Feb. 2009, which is the national phase of PCT application PCT/NL2009/050069 having an international filing date of 16 Feb. 2009, which claims benefit of European patent application No. 08151584.3 filed 18 Feb. 2008. The contents of the above patent applications are incorporated by reference herein in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 313632009910SeqList.txt, date recorded: Dec. 20, 2013, size: 34,658 bytes).

BACKGROUND OF THE INVENTION

The invention relates to the field of microbial production, more specifically production of itaconic acid (itaconate), more specifically production of itaconate in micro-organisms.

Production and metabolism of itaconic acid in microbial cells has been studied extensively for several decades (Calam, C. T. et al., 1939, Thom. J. Biochem., 33:1488-1495; Bentley, R. and Thiessen, C. P., 1956, J. Biol. Chem. 226:673-720; Cooper, R. A. and Kornberg, H. L., 1964, Biochem. J., 91:82-91; Bonnarme, P. et al., 1995, J. Bacteriol. 117:3573-3578; Dwiarti, L. et al., 2002, J. Biosci. Bioeng. 1:29-33), but the metabolic pathway for itaconic acid has not been unequivocally established (Wilke, Th. and Vorlop, K.-D., 2001, Appl. Microbiol. Biotechnol. 56:289-295; Bonnarme, P. et al., 1995, J. Bacteriol. 177:3573-3578). A complicating factor in this respect is that aconitase, the enzyme that interconverts citric acid into cis-aconitate, and vice versa, and other enzymes in the metabolic pathway have been found to be present in many isoforms in microbial cells.

Production of itaconic acid is now commercially achieved in *Aspergillus terreus*, which has physiological similarity to *A. niger* and *A. oryzae*. However, these latter two accumulate citric acid, due to the absence of cis-aconic acid decarboxylase (CAD) activity. Substrates used by these fungi include mono- and disaccharides, such as glucose, sucrose and fructose and starches, as they exist in forms that are degradable by the micro-organism, and molasses. Recently, it has been discovered that also glycerol is a useful substrate in itaconic acid production by *A. terreus* (U.S. Pat. No. 5,637,485).

The general scheme currently envisioned for itaconic acid biosynthesis is given in FIG. 1, wherein clearly the existence of the biosynthetic route both in the cytosol and the mitochondria is depicted and the connection between these two compartments. At several points of this scheme possibilities exist to try to improve the existing commercial production of itaconic acid in micro-organisms.

SUMMARY OF THE INVENTION

The invention comprises a nucleic acid sequence encoding an *Aspergillus* mitochondrial tricarboxylic acid transporter, preferably wherein said nucleic acid sequence comprises the *Aspergillus terreus* nucleic acid sequence ATEG_09970.1, or functional homologues thereof having a sequence identity of at least 55%, preferably 60%, more preferably 70%.

A further embodiment of the invention is a mitochondrial tricarboxylic acid transporter encoded by such a nucleic acid sequence.

Also comprised in the invention is a method for the improved production of itaconic acid, through an increased activity of a protein capable of transporting di/tricarboxylate from the mitochondrion to the cytosol, in a suitable host cell. Preferably said gene encodes a protein that transports tricarboxylate. More preferably the gene encodes a protein that transports cis-aconitate, citrate, and/or isocitrate. Preferably the said gene is derived from *Aspergillus* sp. such as, *Aspergillus terreus*, *Aspergillus niger*, *Aspergillus nidulans*, *Aspergillus oryzae* or *Aspergillus fuminagates*. Preferably, said gene is *Aspergillus terreus* ATEG_09970.1.

According to a further preferred embodiment, the said genes are expressed in a suitable vector, under control of their own or other promoters.

Also comprised in the invention is a method as described above, wherein the transported citrate or isocitrate are further catabolised to cis-aconitate by overexpression of the gene encoding the enzyme(s) catalysing this reaction. Moreover, the invention also comprises a method as described above, wherein the transported or produced cis-aconitate is catabolised to itaconic acid by overexpression of the gene coding for the enzyme CAD (see EP07112895).

Another embodiment of the present invention is formed by a host cell wherein a gene coding for a protein capable of transporting di/tricarboxylate from the mitochondrion to the cytosol, is introduced. Preferably the said gene encodes the above mentioned proteins, and more preferably said gene is *Aspergillus terreus* ATEG_09970.1. A suitable host cell preferably is a host cell selected from filamentous fungi, yeasts and bacteria, more preferably from *Escherichia coli*, *Aspergillus* sp such as (*Aspergillus niger* or *Aspergillus terreus*), citrate-producing hosts or lovastatin producing hosts. The invention further comprises a host cell as described above, wherein the transported or produced cis-aconitate is catabolised to itaconic acid by overexpression of the gene encoding the enzyme CAD.

Further, the invention pertains to the use of the protein(s) transporting di/tricarboxylate for the production of itaconic acid in a suitable host cell. Also comprised in the invention is the use of the protein(s) transporting di/tricarboxylate combined with the CAD enzyme, for the production of itaconic acid in a suitable host cell.

BRIEF DESCRIPTION OF THE DRAWINGS

FIG. 3A-C: Sequence of the *Aspergillus terreus* mitochondrial tricarboxylic acid transporter: FIG. 3A. genomic sequence (SEQ ID NO:1), FIG. 3B. cDNA (SEQ ID NO:2), FIG. 3C. protein sequence (SEQ ID NO:3).

DETAILED DESCRIPTION OF THE INVENTION

Figure 1:
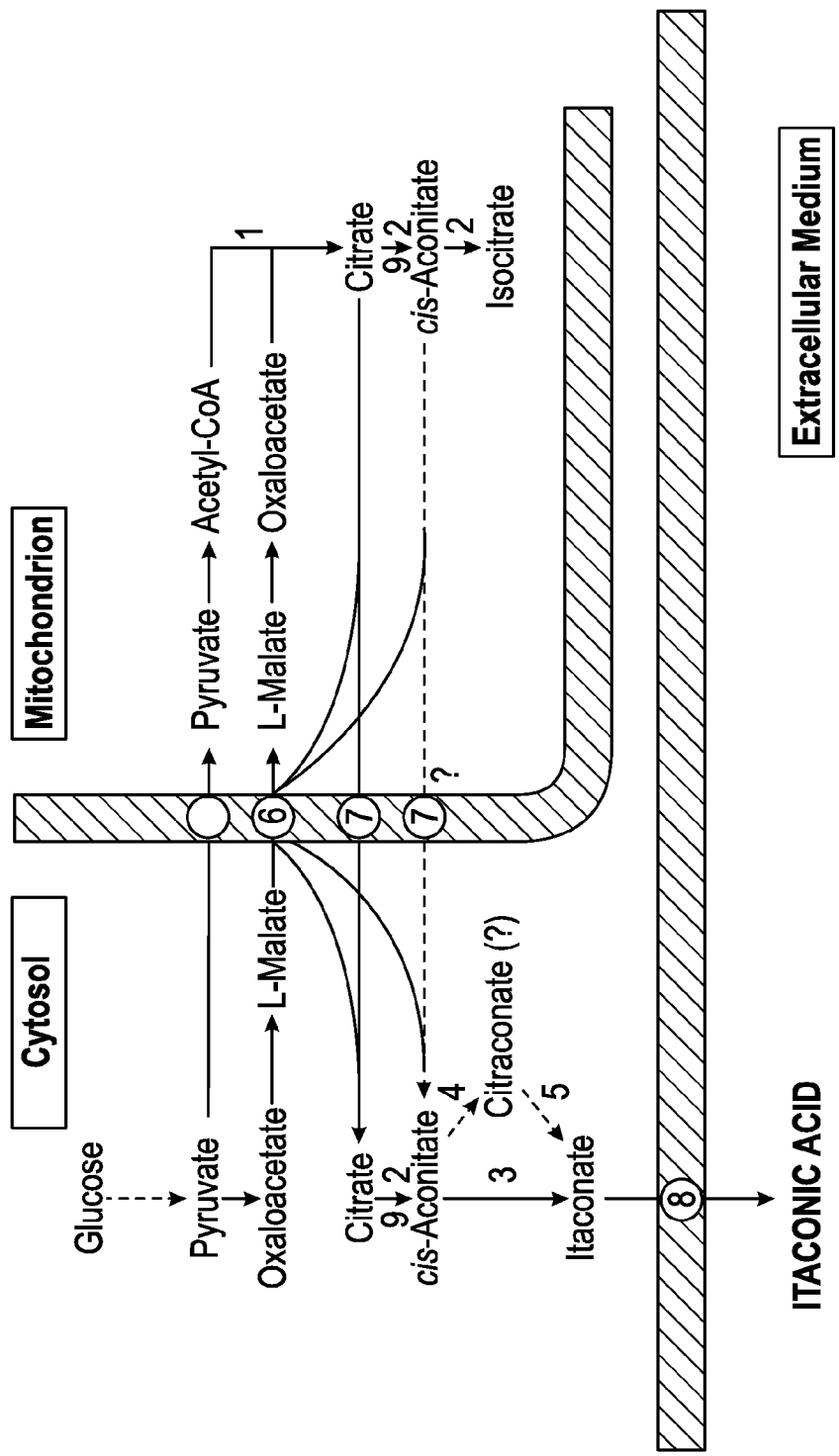
FIG. 1: Postulated biosynthesis route(s) for itaconic acid in *A. terreus*. 1, Citrate synthase; 2, Aconitase; 3, cis-aconitic acid decarboxylase (itaconate-forming); 4, cis-aconitic acid decarboxylase (citraconate-forming); 5, citraconate isomerase; 6, mitochondrial dicarboxylate-tricarboxylate antiporter; 7, mitochondrial tricarboxylate transporter; 8, dicarboxylate transporter; 9, 2-methylcitrate dehydratase.

"Fungi" are herein defined as eukaryotic micro-organisms and include all species of the subdivision Eumycotina (Alexopoulos, C. J., 1962, In: Introductory Mycology, John Wiley & Sons, Inc., New York). The term fungus thus includes both filamentous fungi and yeast. "Filamentous fungi" are herein defined as eukaryotic micro-organisms that include all filamentous forms of the subdivision Eumycotina. These fungi are characterized by a vegetative mycelium composed of chitin, cellulose, and other complex polysaccharides. The filamentous fungi used in the present invention are morphologically, physiologically, and genetically distinct from yeasts. Vegetative growth by filamentous fungi is by hyphal elongation and carbon catabolism of most filamentous fungi are obligately aerobic. "Yeasts" are herein defined as eukaryotic micro-organisms and include all species of the subdivision Eumycotina that predominantly grow in unicellular form. Yeasts may either grow by budding of a unicellular thallus or may grow by fission of the organism.

The term "fungal", when referring to a protein or nucleic acid molecule thus means a protein or nucleic acid whose amino acid or nucleotide sequence, respectively, naturally occurs in a fungus.

The term "gene", as used herein, refers to a nucleic acid sequence containing a template for a nucleic acid polymerase, in eukaryotes, RNA polymerase II. Genes are transcribed into mRNAs that are then translated into protein.

"Expression" refers to the transcription of a gene into structural RNA (rRNA, tRNA) or messenger RNA (mRNA) with subsequent translation into a protein.

The term "vector" as used herein, includes reference to an autosomal expression vector and to an integration vector used for integration into the chromosome.

The term "expression vector" refers to a DNA molecule, linear or circular, that comprises a segment encoding a polypeptide of interest under the control of (i.e., operably linked to) additional nucleic acid segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both. In particular an expression vector comprises a nucleotide sequence that comprises in the 5' to 3' direction and operably linked: (a) a fungal-recognized transcription and translation initiation region, (b) a coding sequence for a polypeptide of interest, and (c) a fungal-recognized transcription and translation termination region. "Plasmid" refers to autonomously replicating extrachromosomal DNA which is not integrated into a microorganism's genome and is usually circular in nature.

An "integration vector" refers to a DNA molecule, linear or circular, that can be incorporated in a microorganism's genome and provides for stable inheritance of a gene encoding a polypeptide of interest. The integration vector generally comprises one or more segments comprising a gene sequence encoding a polypeptide of interest under the control of (i.e., operably linked to) additional nucleic acid segments that provide for its transcription. Such additional segments may include promoter and terminator sequences, and one or more segments that drive the incorporation of the gene of interest into the genome of the target cell, usually by the process of homologous recombination. Typically, the integration vector will be one which can be transferred into the host cell, but which has a replicon which is nonfunctional in that organism. Integration of the segment comprising the gene of interest may be selected if an appropriate marker is included within that segment.

"Transformation" and "transforming", as used herein, refers to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid, or alternatively, may be integrated into the host cell genome.

By "host cell" is meant a cell which contains a vector or recombinant nucleic acid molecule and supports the replication and/or expression of the vector or recombinant nucleic acid molecule. Host cells may be prokaryotic cells such as *E. coli*, or eukaryotic cells such as yeast, fungus, plant, insect, amphibian, or mammalian cells. Preferably, host cells are fungal cells.

Key in the biosynthetic pathway for itaconic acid is the localisation of the various substrates. It is thought that production of itaconic acid mainly occurs in the cytosol (see FIG. 1 and Jaklitsch, W. M. et al., 1991, J. Gen. Microbiol. 137: 533-539). Thus optimal availability of the substrates for the conversion to itaconic acid in the cytosol is required. The present inventors have found the gene that is coding for the transporter that is responsible for transporting the tricarboxylic acids that are substrate for the production of itaconic acid from the mitochondria to the cytosol. Said gene is found to be present on a genomic locus of *Aspergillus terreus* that further comprises putative genes involved in the further enzymatic steps in the pathway for itaconic acid production and lovastatin production. The invention now relates to a method for increasing the production of itaconic acid, by overexpression of genes encoding proteins capable of transporting di/tricarboxylic acids from the mitochondrion to the cytosol, leading to increased production of itaconic acid, in a suitable microorganism. The proteins are further defined as proteins capable of transporting tricarboxylic acids more preferably, cis-aconitate, or its precursor's citrate or isocitrate.

Examples of such transporters are, plant mitochondrial dicarboxylate-tricarboxylate carriers (DTC) capable of transporting dicarboxylic acids and tricarboxylic acids (such as citrate, isocitrate, cis-aconitate and trans-aconitate) (Picault et al. 2002, J. Biol. Chem. 277:24204-24211), and the mitochondrial citrate transport protein (CTP) in *Saccharomyces cerevisiae* capable of transporting tricarboxylates like citrate and isocitrate (Kaplan et al. 1995, J. Biol. Chem. 270:4108-4114). The inventors now found a transporter that is specifically involved in the transport of tricarboxylates for the production of itaconic acid. Said gene is identified as ATEG_09970 and the nucleic acid and amino acid sequences are provided in FIG. 3. The nucleic acid sequence has already been disclosed in Birren, B. W. et al. (Database UniProt: Q0C8L4), in which the gene was annotated as belonging to the mitochondrial carrier family. However, it has not been specified that the protein encoded by said sequence would function as a tricarboxylate transporter for the production of itaconic acid. Further, a highly homologous nucleotide sequence from *Aspergillus terreus* was disclosed in U.S. Pat. No. 6,943,017 as an Acetyl CoA transport gene in the synthesis of lovastatin.

Also provided are functional homologues of the ATEG_09970 sequences, that are 50% or more identical to the sequence of FIG. 3*b*, preferably 60% or more, more preferably 70% or more, more preferably 80% or more, more preferably 90% or more and most preferably 95% or more identical. Functional in the term functional homologues means that the homologous protein has a tricarboxylic transporter function i.e. is able to transport tricarboxylates over the mitochondrial membrane.

The term "sequence identity," as used herein, is generally expressed as a percentage and refers to the percent of amino acid residues or nucleotides, as appropriate, that are identical as between two sequences when optimally aligned. For the purposes of this invention, sequence identity means the sequence identity determined using the well-known Basic Local Alignment Search Tool (BLAST), which is publicly available through the National Cancer Institute/National Institutes of Health (Bethesda, Md.) and has been described in printed publications (see, e.g., Altschul et al., J. Mol. Biol, 215(3), 403-10 (1990)). Preferred parameters for amino acid sequences comparison using BLASTP are gap open 11.0, gap extend 1, Blosum 62 matrix.

Every nucleic acid sequence herein that encodes a polypeptide also, by reference to the genetic code, describes every possible silent variation of the nucleic acid. The term "conservatively modified variants" applies to both amino acid and nucleic acid sequences. With respect to particular nucleic acid sequences, conservatively modified variants refers to those nucleic acids which encode identical or conservatively modified variants of the amino acid sequences due to the degeneracy of the genetic code.

The term "degeneracy of the genetic code" refers to the fact that a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation.

As described above the tricarboxylic acid transporters, transport, among others, cis-aconitate, citrate or isocitrate, leading to an increase in cis-aconitate in the cytosol, which leads to a subsequent increase in itaconic acid production (see FIG. 1). An increased activity of said transporters can be achieved in many ways. One way is overexpression of a gene coding for said activity, preferably said gene is ATEG_09970. Overexpression can be effected in several ways. It can be caused by transforming the micro-organism with a gene coding for the transporter. Alternatively, another method for effecting overexpression is to provide a stronger promoter in front of and regulating the expression of said gene. This can be achieved by use of a strong heterologous promoter or by providing mutations in the endogenous promoter. An increased activity of the transporter can also be caused by removing possible inhibiting regulatory proteins, e.g. that inhibit the expression of such proteins. The person skilled in the art will know other ways of increasing the activity of the above mentioned transporter enzyme.

This process can be even further optimised using a method wherein the transported and produced cis-aconitate is converted to itaconic acid, using overexpression of the gene encoding the enzyme CAD (EC 4.1.1.6). "CAD" is defined as a protein, or a nucleotide sequence encoding for the protein, cis-aconitate decarboxylase (CAD), this further comprises enzymes with similar activities (see EP07112895). The CAD gene is preferably derived from *Aspergillus* sp. like, *Aspergillus terreus, Aspergillus niger, Aspergillus nidulans, Aspergillus oryzae* or *Aspergillus fuminagates*. Most preferably the CAD gene is ATEG_09971.1, derived form the gene cluster that also comprises ATEG_09970 (see FIG. 2).

Figure 2:
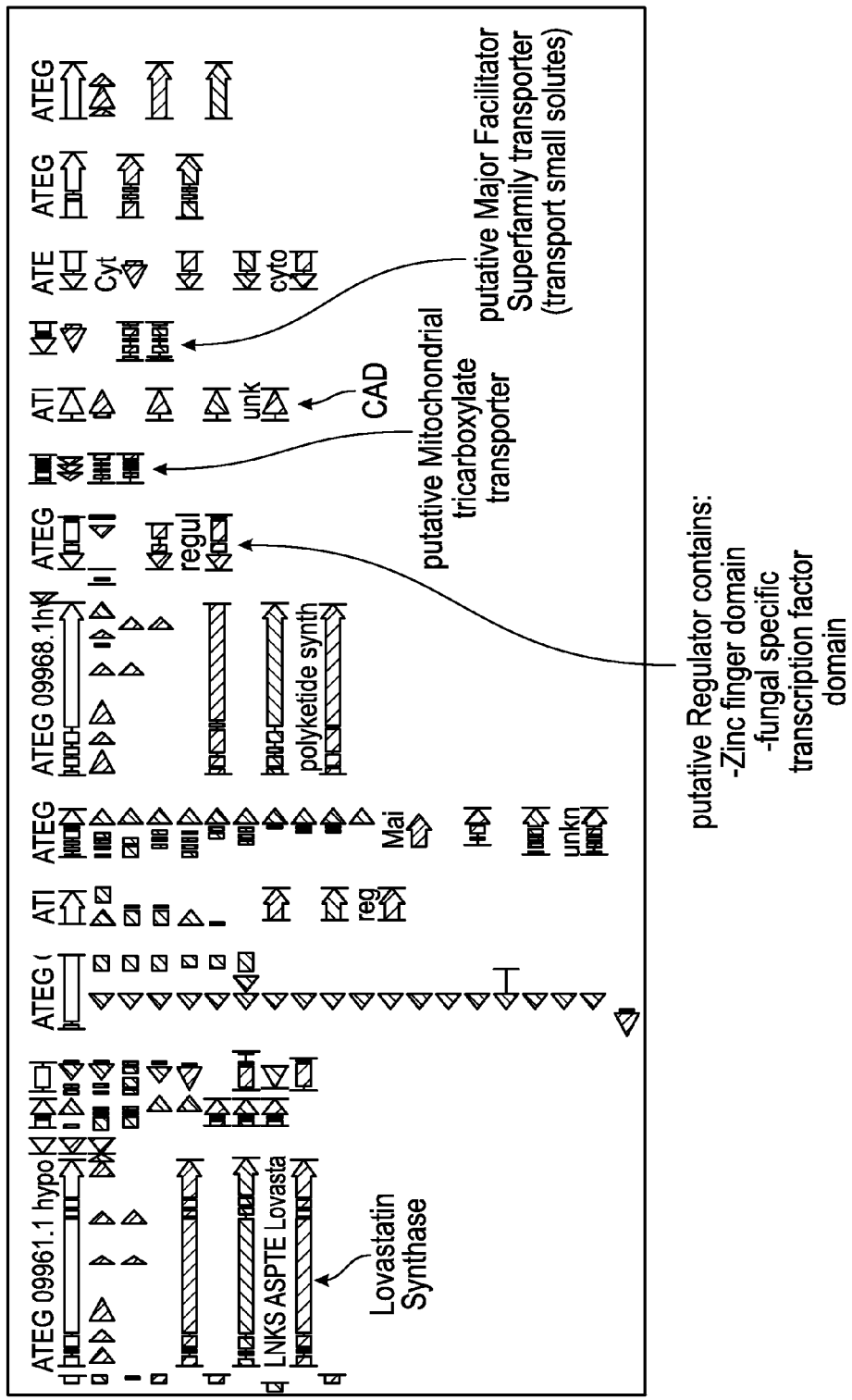
FIG. 2: Overview of the *Aspergillus terreus* genome segment with the cluster of genes involved in production of itaconic acid and lovastatin ranging from ATEG 09961.1-ATEG 09975.1. The cluster contains the cis-aconitate decarboxylase (ATEG_09971.1) and the mitochondrial tricarboxylate transporter (ATEG_9970.1).

Again a further improvement can be achieved by providing a micro-organism with a gene encoding a protein capable of transporting dicarboxylic acids from the cytosol to the extracellular medium, more preferably the major facilitator superfamily transporter that can be found on the gene cluster that also comprises ATEG_09970 (see FIG. 2).

Even further optimisation of the present invention can be achieved by modulating the activity of the regulator protein that comprises a zinc finger and a fungal specific transcription factor domain as can be found on the gene cluster that also comprises ATEG_09970, wherein this regulator protein is indicated as ATEG_09969.1 (see FIG. 2).

In another aspect of the invention, micro-organisms overexpressing at least one but alternatively a combination of the above mentioned nucleotide sequences, encoding at least proteins transporting di/tricarboxylic acids from the mitochondrion to the cytosol, are produced and used, for increased production of itaconic acid. More preferably micro-organisms overexpressing proteins that transport di/tricarboxylates from the mitochondrion to the cytosol combined with overexpressing the CAD enzyme, the major facilitator superfamily transporter and/or the regulator protein as described above are used to further improve the production of itaconic acid.

Micro-organisms used in the invention are preferably micro-organisms that produce itaconic acid. Preferably overexpression of the genes encoding the above described protein(s) and enzyme(s) is accomplished in filamentous fungi, yeasts and/or bacteria, such as, but not limited to, *Aspergillus* sp., such as the fungi *A. terreus, A. itaconicus* and *A. niger, Aspergillus nidulans, Aspergillus oryzae* or *Aspergillus fuminagates, Ustilago zeae, Ustilago maydis, Ustilago* sp., *Candida* sp., *Yarrowia lipolytica, Rhodotorula* sp. and *Pseudozyma antarctica*, the bacterium *E. coli* and the yeast *Saccharomyces cerevisiae*. Especially preferred are homologous or heterologous citric acid producing organisms in which the substrates are available in the host organism.

Recently (see US 2004/0033570) it has also been established that the so-called D4B segment of *Aspergillus terreus*, which comprises the CAD gene is responsible for the synthesis of lovastatin (see FIG. 2). Thus, it is submitted that also these micro-organisms which are known to produce lovastatin would be suitable candidates for the production of itaconic acid. Such micro-organisms include *Monascus* spp. (such as *M. ruber, M. purpureus, M. pilosus, M. vitreus* and *M. pubigerus*), *Penicillium* spp. (such as *P. citrinum, P. chrysogenum*), *Hypomyces* spp., *Doratomyces* spp. (such as *D. stemonitis*), *Phoma* spp., *Eupenicillium* spp., *Gymnoascus* spp., *Pichia labacensis, Candida cariosilognicola, Paecilomyces virioti, Scopulariopsis brevicaulis* and *Trichoderma* spp. (such as *T. viride*). Consequently also the CAD encoding part of the D4B segment and the enzyme with CAD activity for which it codes from these above-mentioned lovastatin producing micro-organisms are deemed to be suitable for use in the present invention. It further is contemplated that a heterologous organism, which in nature does not or hardly produce itaconic acid like *Aspergillus niger*, can be used when providing such an organism with a functional pathway for expression of itaconic acid, by overexpression of the above mentioned genes.

Recombinant host cells described above can be obtained using methods known in the art for providing cells with recombinant nucleic acids. These include transformation, transconjugation, transfection or electroporation of a host cell with a suitable plasmid (also referred to as vector) comprising the nucleic acid construct of interest operationally coupled to a promoter sequence to drive expression. Host cells of the invention are preferably transformed with a nucleic acid construct as further defined below and may comprise a single but preferably comprises multiple copies of the nucleic acid construct. The nucleic acid construct may be maintained episomally and thus comprise a sequence for autonomous replication, such as an ARS sequence. Suitable episomal nucleic acid constructs may e.g. be based on the yeast 2μ or pKD1 (Fleer et al., 1991, Biotechnology 9: 968-975) plasmids. Preferably, however, the nucleic acid construct is integrated in one or more copies into the genome of the host cell. Integration into the host cell's genome may occur at random by illegitimate recombination but preferably the nucleic acid construct is integrated into the host cell's genome by homologous recombination as is well known in the art of fungal molecular genetics (see e.g. WO 90/14423, EP-A-0 481 008, EP-A-0 635 574 and U.S. Pat. No. 6,265,186). Most preferably for homologous recombination the ku70Δ/ku80Δ techniques is used as described for instance in WO 02/052026.

Transformation of host cells with the nucleic acid constructs of the invention and additional genetic modification of the fungal host cells of the invention as described above may be carried out by methods well known in the art. Such methods are e.g. known from standard handbooks, such as Sambrook and Russel (2001) "Molecular Cloning: A Laboratory Manual (3rd edition), Cold Spring Harbor Laboratory, Cold Spring Harbor Laboratory Press, or F. Ausubel et al, eds., "Current protocols in molecular biology", Green Publishing and Wiley Interscience, New York (1987). Methods for transformation and genetic modification of fungal host cells are known from e.g. EP-A-0 635 574, WO 98/46772, WO 99/60102 and WO 00/37671.

In another aspect the invention relates to a nucleic acid construct comprising a nucleotide sequence encoding at least the di/tricarboxylate transporters as defined above and usable for transformation of a host cell as defined above. In the nucleic acid construct, the coding nucleotide sequences preferably is/are operably linked to a promoter for control and initiation of transcription of the nucleotide sequence in a host cell as defined below. The promoter preferably is capable of causing sufficient expression of the di/tricarboxylate transporters and/or the enzyme(s) described above, in the host cell. Promoters useful in the nucleic acid constructs of the invention include the promoter that in nature provides for expression of the coding genes. Further, both constitutive and inducible natural promoters as well as engineered promoters can be used. Promoters suitable to drive expression of the genes in the hosts of the invention include e.g. promoters from glycolytic genes (e.g. from a glyceraldehyde-3-phosphate dehydrogenase gene), ribosomal protein encoding gene promoters, alcohol dehydrogenase promoters (ADH1, ADH4, and the like), promoters from genes encoding amylo- or cellulolytic enzymes (glucoamylase, TAKA-amylase and cellobiohydrolase). Other promoters, both constitutive and inducible and enhancers or upstream activating sequences will be known to those of skill in the art. The promoters used in the nucleic acid constructs of the present invention may be modified, if desired, to affect their control characteristics. Preferably, the promoter used in the nucleic acid construct for expression of the genes is homologous to the host cell in which genes are expressed.

In the nucleic acid construct, the 3'-end of the coding nucleotide acid sequence(s) preferably is/are operably linked to a transcription terminator sequence. Preferably the terminator sequence is operable in a host cell of choice. In any case the choice of the terminator is not critical; it may e.g. be from any fungal gene, although terminators may sometimes work if from a non-fungal, eukaryotic, gene. The transcription termination sequence further preferably comprises a polyadenylation signal.

Optionally, a selectable marker may be present in the nucleic acid construct. As used herein, the term "marker" refers to a gene encoding a trait or a phenotype which permits the selection of, or the screening for, a host cell containing the marker. A variety of selectable marker genes are available for use in the transformation of fungi. Suitable markers include auxotrophic marker genes involved in amino acid or nucleotide metabolism, such as e.g. genes encoding ornithine-transcarbamylases (argB), orotidine-5'-decarboxylases (pyrG, URA3) or glutamine-amido-transferase indoleglycerol-phosphate-synthase phosphoribosyl-anthranilate isomerases (trpC), or involved in carbon or nitrogen metabolism, such e.g. niaD or facA, and antibiotic resistance markers such as genes providing resistance against phleomycin, bleomycin or neomycin (G418). Preferably, bidirectional selection markers are used for which both a positive and a negative genetic selection is possible. Examples of such bidirectional markers are the pyrG (URA3), facA and amdS genes. Due to their bidirectionality these markers can be deleted from transformed filamentous fungus while leaving the introduced recombinant DNA molecule in place, in order to obtain fungi that do not contain selectable markers. This essence of this MARKER GENE FREE™ transformation technology is disclosed in EP-A-0 635 574, which is herein incorporated by reference. Of these selectable markers the use of dominant and bidirectional selectable markers such as acetamidase genes like the amdS genes of A. nidulans, A. niger and P. chrysogenum is most preferred. In addition to their bidirectionality these markers provide the advantage that they are dominant selectable markers that, the use of which does not require mutant (auxotrophic) strains, but which can be used directly in wild type strains.

Optional further elements that may be present in the nucleic acid constructs of the invention include, but are not limited to, one or more leader sequences, enhancers, integration factors, and/or reporter genes, intron sequences, centromers, telomers and/or matrix attachment (MAR) sequences. The nucleic acid constructs of the invention may further comprise a sequence for autonomous replication, such as an ARS sequence. Suitable episomal nucleic acid constructs may e.g. be based on the yeast 2μ or pKD1 (Fleer et al., 1991, Biotechnology 9: 968-975) plasmids. Alternatively the nucleic acid construct may comprise sequences for integration, preferably by homologous recombination (see e.g. WO98/46772). Such sequences may thus be sequences homologous to the target site for integration in the host cell's genome. The nucleic acid constructs of the invention can be provided in a manner known per se, which generally involves techniques such as restricting and linking nucleic acids/ nucleic acid sequences, for which reference is made to the standard handbooks, such as Sambrook and Russel (2001) "Molecular Cloning: A Laboratory Manual (3rd edition), Cold Spring Harbor Laboratory, Cold Spring Harbor Laboratory Press, or F. Ausubel et al, eds., "Current protocols in molecular biology", Green Publishing and Wiley Interscience, New York (1987).

In a further aspect the invention relates to fermentation processes in which the transformed host cells of the invention are used for the conversion of a substrate into itaconic acid. A preferred fermentation process is an aerobic fermentation process. The fermentation process may either be a submerged or a solid state fermentation process.

In a solid state fermentation process (sometimes referred to as semi-solid state fermentation) the transformed host cells are fermenting on a solid medium that provides anchorage points for the fungus in the absence of any freely flowing substance. The amount of water in the solid medium can be any amount of water. For example, the solid medium could be almost dry, or it could be slushy. A person skilled in the art knows that the terms "solid state fermentation" and "semi-solid state fermentation" are interchangeable. A wide variety of solid state fermentation devices have previously been described (for review see, Larroche et al., "Special Transformation Processes Using Fungal Spores and Immobilized Cells", Adv. Biochem. Eng. Biotech., (1997), Vol 55, pp. 179; Roussos et al., "Zymotis: A large Scale Solid State Fermenter", Applied Biochemistry and Biotechnology, (1993), Vol. 42, pp. 37-52; Smits et al., "Solid-State Fermentation—A Mini Review, 1998), Agro-Food-Industry Hi-Tech, March/April, pp. 29-36). These devices fall within two categories, those categories being static systems and agitated systems. In static systems, the solid media is stationary throughout the fermentation process. Examples of static systems used for solid state fermentation include flasks, petri dishes, trays, fixed bed columns, and ovens. Agitated systems provide a means for mixing the solid media during the fermentation process. One example of an agitated system is a rotating drum (Larroche et al., supra). In a submerged fermentation process on the other hand, the transformed fungal host cells are fermenting while being submerged in a liquid medium, usually in a stirred tank fermenter as are well known in the art, although also other types of fermenters such as e.g. airlift-type fermenters may also be applied (see e.g. U.S. Pat. No. 6,746,862).

Preferred in the invention is a submerged fermentation process, which is performed fed-batch. This means that there is a continuous input of feed containing a carbon source and/or other relevant nutrients in order to improve itaconic acid yields. The input of the feed can, for example, be at a constant rate or when the concentration of a specific substrate or fermentation parameter falls below some set point.

It is preferred to use a host cell that naturally would contain the enzymes/transporters of the itaconic acid pathway as depicted in FIG. 1, and the enzymes/transporters of the citric acid pathways in the cytosol and mitochondrion. However, if the host would lack one or more of these genes, they can be co-introduced with the above described enzymes. Such a co-introduction can be performed by placing the nucleotide sequence of such a gene on the same plasmid vector as the above described genes, or on a separate plasmid vector.

Further, since the itaconic acid pathway is located partly in the cytosol and partly in the mitochondrion, it is contemplated that overexpression of the genes/enzymes in either or both of those compartments would be desirable. The person skilled in the art will know how to achieve overexpression in the cytosol or mitochondria by using the appropriate signal sequences.

EXAMPLES

Example 1

Construction of Micro-Array

An anonymous clone/EST-based array approach was taken according to the following scheme:

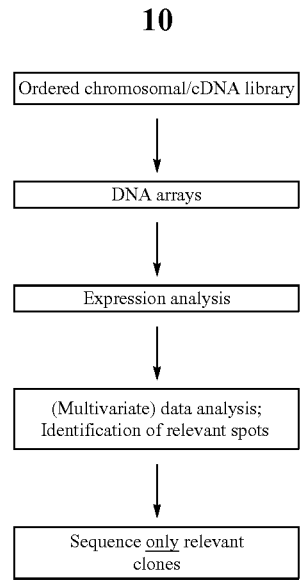

An *A. terreus* micro-array was made composed of a clone-based and an EST-based array.

Materials and Methods Construction Micro-Array

Isolation of Chromosomal DNA from *A. Terreus*

*A. terreus* was cultivated overnight in a shake flask in enriched minimal medium at 33° C. and 250 rpm. Enriched minimal medium (pH 5.5) is mineral medium (MM) supplemented with 0.5% yeast extract and 0.2% casamino acids. The composition of MM was: 0.07 M $NaNO_3$, 7 mM KCl, 0.11 M $KH_2PO_4$, 2 mM $MgSO_4$, and 1 ml/l of trace elements (1000*stock solution: 67 mM $ZnSO_4$, 178 mM $H_3BO_3$, 25 mM $MnCl_2$, 18 mM $FeSO_4$, 7.1 mM $CoCl_2$, 6.4 mM $CuSO_4$, 6.2 mM $Na_2MoO_4$, 174 mM EDTA).

Mycelium was harvested after 22 hours and frozen in liquid nitrogen. Chromosomal DNA was isolated from 4.5 g mycelium following the protocol described below.

Grind 0.5-1.0 g mycelium under liquid nitrogen using the membrane disrupter.

Place polypropylene tubes (Greiner) with 1.5 ml water-saturated phenol, 1 ml TNS, 1 ml PAS and 0.5 ml 5×RNB in a water bath at 55° C., add the still frozen mycelium to the tubes and vortex every 20 seconds for totally 2-4 minutes.

TNS: triisopropyl naphthalene sulphonic acid, 20 mg/ml in water, freshly prepared PAS: 4 aminosalisylic acid, 120 mg/ml in water, freshly prepared 5×RNB: 60.55 g Tris, 36.52 g NaCl, 47.55 g EGTA in 500 ml water (pH=8.5)

Add 1 ml sevag and vortex with intervals for another 1-2 minutes.

Spin for 10 min. in the tabletop centrifuge at 4° C. at maximum velocity.

Extract the water-phase once again with phenol-sevag and twice with sevag. GENTLY, AVOID SHEARING!

Precipitate the DNA with 2 volumes ethanol. Spin directly for 10 min. in the tabletop centrifuge.

Drain the tube, dry it with Kleenex and resuspend the pellet in 500 µl Tris/EDTA. Transfer to a microvial.

Extract with phenol-sevag until interface stays clean. Then extract once with sevag.

Precipitate with 2 volumes ice-cold ethanol, spin down and resuspend the pellet in 100-200 µl TE with 50 µg/ml RNase.

Construction of Clone-Based gDNA Library
  The gDNA library was prepared as follows:
    Chromosomal A. terreus DNA was sheared into fragments of size 1.5-2.5 kb
    The sheared DNA was subsequently size fractionated, end-repaired (Lucigen), and ligated into blunt-end pSMART-HC-Amp vectors (Lucigen).
    The ligated constructs were transformed into E. coli DH10b
    Colony PCR was performed on 96 transformants to check that >90% of the inserts had the correct size
    Sequence analysis (short run) was performed on 20 clones to confirm their diversity and fungal origin
    Colony picking of 20,000 amp-resistant colonies was carried out into 96-well microtiter plates containing TY medium+100 µg/ml ampicillin
  The 20.000 clones were replicated into 96-well microtiter plates. The ordered libraries are stored as glycerol stocks at −80° C.
Generation of mRNA for cDNA Library Construction
  Precultures: A. terreus spores ($10^6$-$10^7$/ml) were inoculated into 100 ml B medium (2 g/l NH4NO3; 1 g/l MgSo4*7H2O; 0.008 g/l ZnSO4*7H2O; 0.015 g/l CuSO4*5H2O; 1.5 ppm FeSO4*5H2O; 0.08 g/l KH2PO4; 10 g/l CaCl2*2H2O, set to pH 3.1 with HCl) containing 20 g/l glucose, and incubated for 24-48 hours at 37° C. at 250 rpm. Production cultures (B medium containing 100 g/l glucose) were inoculated 1/10 (v/v) for 2-days cultivations and 1/25 (v/v) for 3-day cultivations. After 2-3 days cultivation mycelium was harvested, filtered over miracloth, washed with 0.2 M sodium phosphate buffer (pH 6.5), frozen in liquid nitrogen and stored at −80° C.
Isolation of mRNA from A. Terreus
    grind mycelium with mortar and pestle under liquid nitrogen; add 100 µl β-mercaptoethanol before grinding to inactivate RNAse
    transfer powder to cooled plastic tube (1.0 g per tube); keep mycelium frozen
    add 4 ml Trizol and vortex till homogenous
    add 0.4 ml chloroform and vortex
    centrifuge for 20-30 min. at 3700 rpm, 4° C.
    transfer supernatant to Eppendorf tubes (1.2 ml per tube)
    add 0.7 ml per 1.2 ml supernatant
    centrifuge in eppendorf centrifuge for 15 min. at 14.000 rpm, 4° C.
    wash pellet with 1 ml 70% ethanol
    centrifuge 5 min., 14.000 rpm, 4° C.
    air-dry pellet and resuspend in 0.2 ml water
    store RNA samples at −80° C.
Construction of cDNA Library
  The cDNA library was prepared as follows:
    The RNA was run on gel to determine the quality of the sample
    polyT-primed cDNA was prepared from the total RNA provided (RT-PCR reaction using superscript and dT primers
    The cDNA was size fractionated to give fragments of size 1.0-1.5 kb
    The fragments were end-repaired (Lucigen), and ligated into blunt-end pSMART-HC-kan vectors (Lucigen).
    Restriction analysis of 96 clones was performed to check the insert size and the % of transformants which had the correct insert size
    Sequence analysis (short run) of 20 clones was performed to confirm diversity and fungal origin
    5,000 kanamycin-resistant colonies were picked into microtiter plates
  The 5000 cDNA clones were replicated into 96-well microtiter plates. The ordered libraries were stored as glycerol stocks at −80° C.
Construction of the A. Terreus Clone-Based Array
  PCR fragments were generated from the different clones from the gDNA (20,000 clones) and cDNA (5,000 clones) library by mass 96 well PCR (50 µl/well, Lucigen SMART-SR1/SL1 primers with 5'-C6-aminolinkers, SuperTaq and buffer from HT Biotech. Ltd, dNTP's (Roche 11 969 064 001), pintool dipped template from grown colony plates).
  All above PCR products were purified by 96 well precipitation (isopropanol and 96% ethanol wash), speedvac dried, dissolved in 15 µl 3×SSC/well and spotted with quill pins (Telechem SMP3) on CSS100 silylated aldehyde glass slides (Telechem, USA) using a SDDC2 Eurogridder (ESI, Canada). During spotting, aminolinkers of PCR products will covalently link with aldehyde groups of the coated slides.
  gDNA and cDNA PCR products were spotted on two separate slides (slide a: 1st 10,000 gDNA's+5000 cDNA's; slide b: 2nd 10,000 gDNA's+same 5000 cDNA's).
  For the clone-based array a genomic library was constructed. A total of 20,000 clones containing chromosomal fragments was generated, 90% of which had an average insert size of 1.5-2.5 kb. This resulted in a full genome coverage of 64% (Akopyants et al., 2001).
  For the EST-based array a cDNA library of in total 5000 cDNA clones was constructed, 70% of which had an average insert size of 1.0-1.5 kb. This so-called EST-based approach has the advantage that it will be enriched for the genes expressed under the selected (itaconic acid producing) conditions. Moreover, in the EST-based approach per clone (and thus spot) only a single gene is represented in eukaryotes.
  The complete micro-array, thus consisting of 20,000 genomic DNA clones and 5,000 cDNA clones was composed of an A and a B glass slide. Both slides contained the same 5,000 cDNA spots. The A and B slide each contained 10,000 of the gDNA spots.

Example 2

Generation of the Different RNA Samples by Fermentation

Materials and Methods Fermentation and mRNA Isolation
Fermentation Conditions of A. Terreus
  5-Liter controlled batch fermentations were performed in a New Brunswick Scientific Bioflow 3000 fermentors. The following conditions were used unless stated otherwise:
    37° C.
    pH start 3.5 set point 2.3
    DO set points
      Day 1: 75%
      Day 2, 3, 4: 50%
      Subsequent days: 25%
    Preculture: 100 ml of the same medium as used in the fermentation medium ($10^7$ spores/ml) in 500 ml Erlenmeyer flask with baffles, overnight, 37° C., 150 rpm
    pH control: 4M KOH (Base), 1.5 M $H_3PO_4$ (Acid)
    Antifoam: Struktol (Schill & Seilacher)
Fermentation Medium Compositions:
    Per liter: 2.36 g of $NH_4SO_4$, 0.11 g of $KH_2PO_4$, 2.08 g of $MgSO_4*7H_2O$, 0.13 g of $CaCl_2*2H_2O$, 0.074 g of NaCl, 0.2 mg of $CuSO_4*5H_2O$, 5.5 mg of $Fe(III)SO_4.7H_2O$, 0.7 mg of $MnCl_2*4H_2O$ and 1.3 mg of $ZnSO_4*7H_2O$ and 100 g of glucose as a carbon source.

All media were prepared in demineralised water.

Isolation of mRNA from *A. Terreus*

See mRNA isolation protocol described in Example 1

Determination of the Itaconate Concentration by HPLC

5 µl of a 10-times diluted supernatant sample (split ratio 1:3) was separated using a Waters 2695 Separations module on a reversed-phase Develosil 3 µm RP-Aqueous C30 140A column (150×3 mm) (Phenomenex p/n CH0-6001) at 25° C. using the solvent gradient profile (flow rate was 0.4 ml/min) shown in Table 1.

TABLE 1

Solvent gradient of the RP-UV method.

| Time (min) | A (20 mM $NaH_2PO_4$ pH 2.25) (%) | B (Acetonitril) (%) |
|---|---|---|
| 0 | 100 | 0 |
| 10 | 100 | 0 |
| 15 | 95 | 5 |
| 20 | 95 | 5 |
| 21 | 100 | 0 |
| 30 | 100 | 0 |

Compounds were detected by UV at 210 nm using a Waters 2487 Dual wavelength Absorbance detector (Milford, MA, USA).

Itaconate Productivity

Itaconate productivity at a certain time point was calculated as the slope of the regression line between that particular time point and the time points right before and after that time point. To this end of 6-10 supernatant samples of the different fermentations, the itaconate concentrations were determined by HPLC.

For the transcriptomics approach it is essential to have RNA samples from fermentations that result in the production of different amounts of itaconate. Therefore a literature survey was performed in order to identify medium components and/or physicochemical conditions that affect the amount of itaconate produced by *A. terreus*. Although many conflicting reports were found regarding the effect that a specific parameter has on itaconic acid production, 4 key overall parameters were identified from this literature survey, i.e. (i) carbon source, (ii) pH, (iii) trace element (i.e. Mn) concentration and (iv) oxygen tension. Fermentations with *A. terreus* varying principally in these four parameters were performed on a mineral salts medium to ensure that the elemental limitations required for itaconate production would be achieved. Table 2 presents an overview of the fermentations performed in this study.

TABLE 2

Overview of the fermentations performed in order to generate RNA samples for transcriptome analysis. The reference fermentation is on 100 g/l glucose, dO2, day 1, 75%; day 2-4, 50%, day 5 and further 25%, pH start 3.5, set point at 2.3.

| Fermentation run | Fermentation | Environmental condition | Max. Itaconic acid (g/l) | Max. Biomass (gDWT/kg) |
|---|---|---|---|---|
| First Run | 1 | Glucose (100 g/l) (control) | 16.1 | 12.7 |
| | 2 | Fructose as C-source | 8.84 | 13.7 |
| | 3 | Maltose as C-source | 13.9 | 12.1 |
| Second run | 4 | Glucose (100 g/l) pH start 3.5, set point 2.3 (control) | 25.8 | 11.6 |
| | 5 | pH set 3.5 | 8.7 | 16.5 |
| | 6 | pH start 3.5 no set point | 30.6 | 8.7 |
| Third run | 7 | Low glucose (30 g/l) | 11.1 | 6.7 |
| | 8 | $O_2$ set point 25% | 47.2 | 12.0 |
| | 9 | 5* higher Mn | 20.3 | 13.8 |
| Fourth run | 10 | Glucose (100 g/l) (control) | 26.9 | 17.9 |
| | 11 | pH set 4.5 | 0.1 | 20.4 |
| | 12 | $O_2$ set point 10% | 52.9 | 10.6 |

As shown in Table 2, a considerable variation in the amount of itaconate is produced in this set of fermentations, ranging from almost no itaconate (fermentation #11; pH 4.5) to about 50 g/l itaconate (#8 and #12; $O_2$ set point 25% and 10% respectively).

Of each fermentation 2 to 5 samples were harvested for isolation of mRNA.

From in total 23 fermentation samples mRNA could be isolated. Of 7 samples, mRNA was isolated twice independently. It proved to be especially difficult (impossible) to extract RNA from the samples taken in the stationary phase. A number of samples showed partial degradation of the RNA. Although no mRNA could be isolated from the samples from fermentations #6 and #12, the remaining samples still covered the complete range of itaconate production (Table 3).

TABLE 3

List of 30 mRNA samples from various fermentation conditions that were used for transcriptome analysis.

| Sample no. | Fermentation condition | RNA id | EFT (hours) | Itaconic acid (g/l) | Productivity | RNA quality |
|---|---|---|---|---|---|---|
| R3 | gluc100 | 1.3.a | 50.3 | 14.6 | 0.117 | ok |
| R4 | gluc100 | 1.4.a | 74.8 | 16.1 | 0.060 | ok |
| R5 | fruc100 | 2.3.a | 50.3 | 8.2 | 0.082 | ok |
| R6 | fruc100 | 2.3.b | 50.3 | 8.2 | 0.082 | ok |
| R7 | fruc100 | 2.4.a | 75.05 | 8.6 | −0.013 | ok |
| R8 | malt100 | 3.3.a | 50.3 | 7 | 0.355 | ok |
| R9 | malt100 | 3.4.a | 75 | 12.1 | 0.220 | ok |
| R10 | pH-i3.5 | 4.3.a | 53.25 | 25.8 | 0.146 | part degr |
| R11 | pH-i3.5 | 4.3.b | 53.25 | 25.8 | 0.146 | part degr |
| R12 | pH-i3.5 | 4.4.a | 73 | 24 | −0.153* | ok |
| R13 | pH-c3.5 | 5.3.a | 53.5 | 7.5 | −0.042 | ok |
| R14 | pH-c3.5 | 5.3.b | 53.5 | 7.5 | −0.042 | ok |
| R15 | pH-c3.5 | 5.4.a | 73.25 | 7.9 | 0.035 | ok |
| R16 | gluc30 | 7.2.a | 30.25 | 9 | 0.317 | ok |
| R1 | gluc30 | 7.3.a | 43.5 | 10 | 0.030 | ok |
| R17 | gluc30 | 7.3.a | 43.5 | 10 | 0.030 | ok |
| R18 | O2s25% | 8.2.a | 30.5 | 36* | 0.824* | ok |
| R19 | O2s25% | 8.4.a | 78.25 | 46 | 0.029 | part degr |
| R20 | 5xMn | 9.2.a | 30.75 | 1 | 0.194 | ok |
| R21 | 5xMn | 9.2.b | 30.75 | 1 | 0.194 | ok |
| R22 | 5xMn | 9.3.a | 53.5 | 10 | 0.496 | part degr |
| R23 | 5xMn | 9.3.b | 53.5 | 10 | 0.496 | part degr |
| R24 | 5xMn | 9.4.a | 78.5 | 19 | 0.189 | part degr |
| R25 | 5xMn | 9.4.b | 78.5 | 19 | 0.189 | part degr |
| R26 | 5xMn | 9.5.a | 93.25 | 20 | 0.106 | ok |
| R2 | Gluc100 | 10.3.a | 51.5 | 14.7 | 0.256 | ok |
| R27 | Gluc100 | 10.3.a | 51.5 | 14.7 | 0.256 | ok |
| R28 | Gluc100 | 10.4.a | 74 | 19.5 | 0.085 | ok |
| R29 | Gluc100 | 10.5.a | 100.4 | 22 | 0.177 | part degr |
| R30 | Gluc100 | 10.5.b | 100.4 | 22 | 0.177 | part degr |

TABLE 3-continued

List of 30 mRNA samples from various fermentation conditions that were used for transcriptome analysis.

| Sample no. | Fermentation condition | RNA id | EFT (hours) | Itaconic acid (g/l) | Productivity | RNA quality |
|---|---|---|---|---|---|---|
| R31 | pH 4.5 | 11.3.a | 51.5 | 0.04* | −0.001 | ok |
| R32 | pH 4.5 | 11.4.a | 74 | 0.05* | 0.003 | ok |

The samples marked with asterix were the samples used for the differential expression data analysis.

Example 3

Transcriptome Analysis, Data Analysis of the Array Data

Materials and Methods Transcriptome Analysis, Data Normalization and Data Analysis
Labeling of RNA and gDNA Total RNA's (5 μg/30 μl reaction), isolated from various *A. terreus* cultures (strain NRRL 1960, BASF) with differential itaconate production, were labelled with amino-allyl-dUTP (0.75 μM aa-dUTP final conc., Sigma A0410), using 3 μl 50 μM oligo p(dT)$_{15}$ primer (La Roche, 814270), unlabelled dNTP's (added to 1.25 μM final conc. for each dNTP), 2 μl Superscript II Reverse Transcriptase and buffer (Life Technologies, 10297-018: primer annealing 10 min 70° C., transcriptase 180 min 42°). After RNA hydrolysis (3 μl 2.5M NaOH, 30 min 37°, 3 μl 2.5 M HAc) the aa-dUTP labelled cDNA was directly purified (below).

As a reference for correcting slide differences (spotting, labeling-, hybridization- and scan efficiency), gDNA (0.5 μg/reaction) of *Aspergillus terreus* (strain NRRL 1960, BASF) was labelled with aa-dUTP, using dNTP's (conc. as above), Klenov-DNA Polymerase and buffer (Bioprime kit, Invitrogen 18094-011: primer annealing 5 min 96° C., polymerase 90 min 37°).

The aa-dUTP-labelled cDNA or gDNA was purified (QIAquick column, Qiagen 28106), speedvac dried, dissolved (4.5 μl 0.1 M Na$_2$CO$_3$), coupled with 4.5 μl Cy5-NHS-ester for cDNA, or 4.5 μl Cy3-NHS-ester for gDNA (Amersham/GE-Healthcare PA25001 or PA23001 respectively, each in 73 μl DMSO) for 60 min at 20° C., diluted with 10 μl of water, and again purified on Autoseq G50 columns (GE-Healthcare 27-5340).
Array Blocking, (Pre)Hybridization and Image Analysis Before hybridization with the array produced as described above, slides were blocked (removal surplus of spotted PCR products and blocking of free aldehyde groups) by 3× quickly washing (20° C.) with Prehyb buffer and 45 min incubation (42° C.) in PreHyb buffer (5×SSC, 1% BSA, 0.1% SDS). After 4 washes in water, spotted PCR products were denatured by dipping the slides 5 sec in boiling water and drying them with a N$_2$-gas-pistol.

The Cy5- and Cy3-labelled sample were combined, 8 μl 25 μg/μl yeast tRNA (Invitrogen, 15401-029) and 4 μl 5 μg/μl poly-dA/dT (Amersham 27-7860) were added, the mixture was speed vac dried, dissolved in 160 μl Easyhyb buffer (Roche, 1 796 895), denatured (2 min, 96° C.), cooled to 50° C., applied on a pair of prehybridised slides (a+b, 80 μl/slide) prewarmed at 50° C., covered with a cover slide (Hybri slibs, Mol. Probes. H-18201) and incubated overnight at 42° C. in a humidified hybridization chamber (Corning 2551). Slides were washed (pair a+b in one 50 ml tube, 1× in 1×SSC/0.1% SDS 37° C., 1× in 0.5×SSC 37° C., 2× in 0.2×SSC 20° C.) and dried with N$_2$-gas. All pre-hybridisation buffers were 0.45 μm filtered to reduce dust noise. Slide images of Cy5- and Cy3 fluorescence intensity (ScanArray Express Scanner & Software, Packard Biosc.) were analysed (Imagene 5.6 Software, Biodiscovery) to obtain for each spot signal- and local background value (medians) for the hybridized Cy5-RNA and Cy3-reference gDNA. These values were used for further data analysis.
Array Data Normalization Before normalization, all low abundant spots having a Signal/Background below 1.5 were removed. Data were normalized using a total cDNA signal correction. For each slide and each spot, the difference between signal and background was calculated for Cy5 and Cy3. Per slide, the sum of the differences was taken for Cy5 and Cy3, and the ratio between these two was used as normalisation factor for that particular slide. All spots (chromosomal and genomic) were normalised using this total cDNA signal.
Data Analysis of the Transcriptomics Data by Differential Expression Analysis The differential expression value was calculated by dividing the Cy5 (RNA)/Cy3 (gDNA) ratio of a spot in the slide with the highest titer or productivity by the Cy5 (RNA)/Cy3 (gDNA) ratio of that same spot in the slide with the lowest titer or productivity. The samples used for the differential expression analysis are marked in Table 2. The spots were subsequently ranked based on this ratio or, when the ratio was <1, i.e. in the case of down-regulated genes, on 1/ratio.
Sequence Analysis of Spots Selected after Transcriptomics Approach The relevant clones were selected from the glycerol stocks of the ordered libraries (gDNA and cDNA library respectively) and cultivated in 96-well microtiter plates. The sequences of the inserts from both the 3' and the 5' end were determined by High Throughput (HT) sequencing service.

All RNA samples were labelled with Cy5. Hybridisations were performed with all 30 RNA samples, using Cy3-labeled chromosomal DNA of *A. terreus* as the reference.

The raw transcriptomics data were shown to be of high quality, based on visual inspection of the arrays after fluorescence scanning. Notably, also the hybridization with the partially degraded RNA samples gave good results.

The normalized data were subsequently combined. As the *A. terreus* array consisted out of two slides, different strategies of combining the data from the two slides were pursued, making use of the fact that the cDNA clones are present on both the A and B slide:
  SET 1=mean expression signal of the cDNA clones on slide A and B, take only those spots that give a signal on both the A and B slide
  SET 2=use only the signal of the cDNA spots on the A slide. Spots with a Signal/Background below 1.5 were removed.
  SET 3=use only the signal of the cDNA spots on the B slide. Spots with a Signal/Background below 1.5 were removed.
  SET 4=Combimean cDNA data of both the A and B slide;
    i. If both measurement values were zero the combined value was zero;
    ii. If both measurements values were both non-zero, the combined value was equal to the average of the two measurement values;
    iii. If one of the two measurement values was zero and the other measurement value was non-zero, the combined value was equal to the non-zero measurement value.

SET 5=SET 1+normalized gDNA spots using the normalization factor calculated based on the cDNA clones.

The most relevant spots were subsequently identified by differential expression analysis: the expression ratios between the sample with the lowest itaconate titer and the sample with the highest itaconate titer were calculated (see Table 2). As two samples have a low itaconate titer, the differential expression analysis was performed separately with both these reference samples (i.e. sample 3.a and 4.a). Similarly, also the expression ratios between the samples with the lowest and the samples with the highest itaconate productivity were calculated.

'Top 20'-ies of the individual data set using the different data analysis approaches were generated. These 'top-20'-ies were combined, and unique spots were identified (Table 4 and 5). In total 88 spots obtained after the differential analyses (based on 15 models; 5 data sets-2 titer and 1 productivity model) were selected for sequencing.

Of the selected spots, >92% were spots belonging to cDNA clones. Of the differential spots, some 50-75% of the spots were present in the 'top 20' of both the itaconate titer and itaconate productivity differentials lists and were mostly upregulated spots, indicating that they might be really relevant for itaconate production.

Following sequence analysis of the 190 selected spots, the genes present on these inserts were identified by performing a homology search using BLAST based on the draft version of the *A. terreus* genome sequence as available from the BROAD institute (http://www.broad.mit.edu/annotation/fgi/).

Tables 4 and 5 show the results of the genes identified on the 20 highest overall ranking spots identified by differential expression analysis based on titer and productivity, respectively.

TABLE 4

Overall Top 20 Differential expression - itaconic acid titer.

| Rank | Clone ID | Gene locus | Gene name according to (http://www.broad.mit.edu/) |
|---|---|---|---|
| 1 | AsTeR037B09 | ATEG_09971.1 | cis-aconitate decarboxylase |
| 2 | AsTeR017E03 | ATEG_09970.1 | predicted protein |
| 3 | AsTeR008F12 | ATEG_09971.1 | cis-aconitate decarboxylase |
| 4 | AsTeR017E02 | ATEG_09970.1 | predicted protein |
| 5 | AsTeR026D10 | | |
| 6 | AsTeR020B12 | ATEG_09970.1 | predicted protein |
| 7 | AsTeR027F02 | ATEG_09970.1 | predicted protein |
| 8 | AsTeR031E12 | | |
| 9 | AsTeR041A01 | | |
| 10 | AsTeR036C11 | | |
| 11 | AsTeR025E11 | | |
| 12 | AsTeR008H08 | ATEG_09970.1 | predicted protein |
| 13 | AsTeR028C10 | ATEG_09970.1 | predicted protein |
| 14 | AsTeR026G08 | ATEG_09970.1 | predicted protein |
| 15 | AsTeR009E09 | ATEG_09971.1 | cis-aconitate decarboxylase |
| 16 | AsTeR005D11 | ATEG_09971.1 | cis-aconitate decarboxylase |
| 17 | AsTeR056A03 | | |
| 18 | AsTeR010E04 | ATEG_09970.1 | predicted protein |
| 19 | AsTeR045C03 | ATEG_09970.1 | predicted protein |
| 20 | AsTeR054H08 | ATEG_09970.1 | predicted protein |

TABLE 5

Overall Top 20 Differential expression - itaconic acid productivity.

| Rank | Clone ID | Gene locus | Gene name according to (http://www.broad.mit.edu/) |
|---|---|---|---|
| 1 | AsTeR020B12 | ATEG_09970.1 | predicted protein |
| 2 | AsTeR031E12 | | |
| 3 | AsTeR026D10 | | |
| 4 | AsTeR005D11 | ATEG_09971.1 | cis-aconitate decarboxylase |
| 5 | AsTeR017E03 | ATEG_09970.1 | predicted protein |
| 6 | AsTeR008F12 | ATEG_09971.1 | cis-aconitate decarboxylase |
| 7 | AsTeR017E02 | ATEG_09970.1 | predicted protein |
| 8 | AsTeR037B09 | ATEG_09971.1 | cis-aconitate decarboxylase |
| 9 | AsTeR027F02 | ATEG_09970.1 | predicted protein |
| 10 | AsTeR038F06 | | |
| 11 | AsTeR008H08 | ATEG_09970.1 | predicted protein |
| 12 | AsTeR022C05 | ATEG_09971.1 | cis-aconitate decarboxylase |
| 13 | AsTeR037B09 | ATEG_09971.1 | cis-aconitate decarboxylase |
| 14 | AsTeR004A12 | | |
| 15 | AsTeR018E11 | ATEG_09971.1 | cis-aconitate decarboxylase |
| 16 | AsTeR045C03 | ATEG_09970.1 | predicted protein |
| 17 | AsTeR045F08 | ATEG_09970.1 | predicted protein |
| 18 | AsTeR011A05 | | |
| 19 | AsTeR044F02 | ATEG_09970.1 | predicted protein |
| 20 | AsTeR041B02 | | |

Standing out when comparing the highest ranking genes found by differential expression analysis based on productivity versus titer are the cis-aconitate decarboxylase (ATEG_09971.1), and the immediately flanking gene encoding a predicted protein (ATEG_09970.1), both of which are present on multiple clones in the top 20 rankings, underlining their relevance to the itaconate production phenotype.

Example 4

Homology Analysis of the ATEG_09970.1 Gene

A BLAST search was performed in order to identify homologous to the predicted protein ATEG_09970.1 (Table 6). High homologies were only found with genes from two other *A. terreus* strains. With other micro-organisms and more specifically fungi, homologues were found although with low homology. These low identities suggest that this gene is part of a unique pathway. Based on the annotation of these homologous genes ATEG_09970.1 was identified as a putative mitochondrial tricarboxylate transporter.

TABLE 6

BLAST search results with ATEG_09970.1

| Rank | Protein | Best Hit | E value | Identity/Similarity |
|---|---|---|---|---|
| 1 | Predicted protein | XP_001209272.1 *A. terreus* | 1e-173 | 100%/100% |
| 2 | unknown | AAD34562.1 *A. terreus* | 1e-171 | 98%/99% |
| 3 | Conserved hypothetical protein | XP_001219399.1 *C. globosum* | 6e-59 | 43%/60% |
| 4 | Conserved hypothetical protein | XP_360936.2 *M. grisea* | 3e-58 | 44%/62% |
| 5 | Conserved hypothetical protein | XP_001586805.1 *S. sclerotiorum* | 1e-56 | 44%/64% |
| 6 | Mitochondrial tricarboxylate transporter | XP001270567.1 *A. Clavatus* | 7e-56 | 43/62% |
| 7 | Tricarboxylate transport protein | XP_956064.2 *N. Crassa* | 1e-55 | 44%/61% |

TABLE 6-continued

BLAST search results with ATEG_09970.1

| Rank | Protein | Best Hit | E value | Identity/ Similarity |
|---|---|---|---|---|
| 8 | Mitochondrial tricarboxylate transporter | XP_001263903.1 N. Fischeri | 1e-55 | 42%/66% |
| 9 | Mitochondrial tricarboxylate transporter | XP_755059.2 A. Fumigatus | 2e-55 | 42%/62% |
| 10 | Hypothetical protein | XP_001395080.1 A. Niger | 6e-55 | 41%/61% |

It appears that at least the gene coding for the cis-aconitate decarboxylase (ATEG_09971.1) and the gene encoding the putative mitochondrial tricarboxylate transporter (ATEG_09970.1) lie in the same cluster in the *A. terreus* genome (FIG. 2).

Flanking the CAD and the putative mitochondrial tricarboxylate transporter genes is the Major Facilitator Superfamily (MFS) transporter (ATEG_09972.1) (SEQ ID NOS:12-13) that was identified by Partial Least Squares (PLS) biostatistical analysis. MFS transporters are a diverse family of transport proteins, transporting compounds ranging from sugars to organic acids, including dicarboxylic acids. In *A. niger* some 450 different MFS genes are present. The localization of MFS ATEG_09972.1 and its identification by PLS, suggest that this is the itaconate exporter.

A gene neighbouring CAD, the putative mitochondrial tricarboxylate transporter and the putative itaconate exporter is a putative regulator containing a zinc-finger domain (ATEG_09969.1). This gene was not identified using our transcriptomics approach, but considering its localization it is supposed that it is relevant for itaconic acid synthesis FIG. 2 shows that also the lovastatin pathway genes are located on this cluster, suggesting a link between both pathways which are (mainly) specific for *A. terreus*.

Example 5

(Co-)Expression of the ATEG_09970.1 Gene in *Aspergillus niger*

In order to unambiguously establish that the ATEG 9970 protein aids to the increased production of itaconic acid, a naturally non-itaconic acid producing fungal host was (co-) transformed with the CAD gene and the ATEG_09970.1 (MTT) gene.

Expression of the CAD (ATEG 09971.1) Gene in *Aspergillus niger*

A PCR generated copy of the gene encoding the CAD protein (see EP07112895) was generated. For this purpose two sets of primers were generated as shown below. PCR amplification based on *A. terreus* NRRL1960 genomic DNA resulted in the isolation of PCR fragments from which the complete coding region of the gene encoding the CAD protein, could be isolated as BspHI-BamHI fragments.

```
                                        (SEQ ID NO: 4, without intron, 1473 bp)
CAD full sequence 1529 bp
ORIGIN
                                        (SEQ ID NO: 6)
    BspHI  cadfor40° C.
5'-ATCGTCATGACCAAGCAATCTG- 3'

(SEQ ID NO: 7)
    BspHI  cadfor53° C.
5'-ATCGTCATGACCAAGCAATCTGCGGACA-3'

1 ATGACCAAGC AATCTGCGGA CAGCAACGCA AAGTCAGGAG TTACGTCCGA AATATGTCAT

61 TGGGCATCCA ACCTGGCCAC TGACGACATC CCTTCGGACG TATTAGAAAG AGCAAAATAC

121 CTTATTCTCG ACGGTATTGC ATGTGCCTGG GTTGGTGCAA GAGTGCCTTG GTCAGAGAAG

181 TATGTTCAGG CAACGATGAG CTTTGAGCCG CCGGGGGCCT GCAGGGTGAT TGGATATGGA

241 CAGgtaaatt ttattcactc tagacggtcc acaaagtata ctgacgatcc ttcgtatagA
                          (intron)

301 AACTGGGGCC TGTTGCAGCA GCCATGACCA ATTCCGCTTT CATACAGGCT ACGGAGCTTG

361 ACGACTACCA CAGCGAAGCC CCCCTACACT CTGCAAGCAT TGTCCTTCCT GCGGTCTTTG

421 CAGCAAGTGA GGTCTTAGCC GAGCAGGGCA AAACAATTTC CGGTATAGAT GTTATTCTAG

481 CCGCCATTGT GGGGTTTGAA TCTGGCCCAC GGATCGGCAA AGCAATCTAC GGATCGGACC

541 TCTTGAACAA CGGCTGGCAT TGTGGAGCTG TGTATGGCGC TCCAGCCGGT GCGCTGGCCA

601 CAGGAAAGCT CTTCGGTCTA ACTCCAGACT CCATGGAAGA TGCTCTCGGA ATTGCGTGCA

661 CGCAAGCCTG TGGTTTAATG TCGGCGCAAT ACGGAGGCAT GGTAAAGCGT GTGCAACACG

721 GATTCGCAGC GCGTAATGGT CTTCTTGGGG GACTGTTGGC CCATGGTGGG TACGAGGCAA

781 TGAAAGGTGT CCTGGAGAGA TCTTACGGCG GTTTCCTCAA GATGTTCACC AAGGGCAACG

841 GCAGAGAGCC TCCCTACAAA GAGGAGGAAG TGGTGGCTGG TCTCGGTTCA TTCTGGCATA

901 CCTTTACTAT TCGCATCAAG CTCTATGCCT GCTGCGGACT TGTCCATGGT CCAGTCGAGG
```

```
 961 CTATCGAAAA CCTTCAGGGG AGATACCCCG AGCTCTTGAA TAGAGCCAAC CTCAGCAACA
1021 TTCGCCATGT TCATGTACAG CTTTCAACGG CTTCGAACAG TCACTGTGGA TGGATACCAG
1081 AGGAGAGACC CATCAGTTCA ATCGCAGGGC AGATGAGTGT CGCATACATT CTCGCCGTCC
1141 AGCTGGTCGA CCAGCAATGT CTTTTGTCCC AGTTTTCTGA GTTTGATGAC AACCTGGAGA
1201 GGCCAGAAGT TTGGGATCTG GCCAGGAAGG TTACTTCATC TCAAAGCGAA GAGTTTGATC
1261 AAGACGGCAA CTGTCTCAGT GCGGGTCGCG TGAGGATTGA GTTCAACGAT GGTTCTTCTA
1321 TTACGGAAAG TGTCGAGAAG CCTCTTGGTG TCAAAGAGCC CATGCCAAAC GAACGGATTC
1381 TCCACAAATA CCGAACCCTT GCTGGTAGCG TGACGACGA ATCCGGGTG AAAGAGATTG
1441 AGGATCTTGT CCTCGGCCTG GACAGGCTCA CCGACATTAG CCCATTGCTG GAGCTGCTGA
1501 ATTGCCCCGT AAAATCGCCA CTGGTATAA
```

(SEQ ID NO: 8)
```
              cadrev42° C. BamHI
      3'-TTTAGCGGTGACCATATTCCTAGGCCCT-5'
```

(SEQ ID NO: 9)
```
             cadrev52° C. BamHI
      3'-GGCATTTTAGCGGTGACCATATTCCTAGGCCCC-5'
```

(SEQ ID NO: 5)

Translation of CAD encoding gene
Total amino acid number: 490, MW = 52710

```
  1 M T K Q S A D S N A K S G V T S E I C H
 21 W A S N L A T D D I P S D V L E R A K Y
 41 L I L D G I A C A W V G A R V P W S E K
 61 Y V Q A T M S F E P P G A C R V I G Y G
 81 Q K L G P V A A A M T N S A F I Q A T E
101 L D D Y H S E A P L H S A S I V L P A V
121 F A A S E V L A E Q G K T I S G I D V I
141 L A A I V G F E S G P R I G K A I Y G S
161 D L L N N G W H C G A V Y G A P A G A L
181 A T G K L F G L T P D S M E D A L G I A
201 C T Q A C G L M S A Q Y G G M V K R V Q
221 H G F A A R N G L L G G L L A H G G Y E
241 A M K G V L E R S Y G G F L K M F T K G
261 N G R E P P Y K E E E V V A G L G S F W
281 H T F T I R I K L Y A C C G L V H G P V
301 E A I E N L Q G R Y P E L L N R A N L S
321 N I R H V H V Q L S T A S N S H C G W I
341 P E E R P I S S I A G Q M S V A Y I L A
361 V Q L V D Q Q C L L S Q F S E F D D N L
381 E R P E V W D L A R K V T S S Q S E E F
401 D Q D G N C L S A G R V R I E F N D G S
421 S I T E S V E K P L G V K E P M P N E R
441 I L H K Y R T L A G S V T D E S R V K E
461 I E D L V L G L D R L T D I S P L L E L
481 L N C P V K S P L V *
```

The resulting BspHI-BamHI fragment was cloned into the *Aspergillus* expression vector pAN52-4-amdS, based on *Aspergillus* expression vector pAN52-4. The *Aspergillus* expression vector pAN52-4-amdS was derived by cloning the *Aspergillus* selection marker amdS into the *Aspergillus* expression vector pAN52-4 (EMBL accession #Z32699).

Subsequently, an *Aspergillus niger* strain AB1.13 (Mattern, I. E. et al., 1992, Mol. Gen. Genet. 234:332-336) was transformed with the CAD expression vector. AmdS transformants resulting for this experiment were purified by single colony purification and retested for their AmdS+ phenotype.

Co-Expression of the CAD Gene and the ATEG 09970.1 Gene in *Aspergillus niger*

The ATEG_09970.1 gene (MTT) was synthesized (GeneArt®) and cloned into the *Aspergillus niger* expression vector pAN52-5doubleNotI by restriction enzyme cutting sites of double NotI. The expression vector pAN52-5doubleNotI was derived by adding an extra NotI site in the *Aspergillus* expression vector pAN52-4 (EMBL accession #Z32699). Moreover, the codons of the clone were optimized for expression in the *Aspergillus niger* strain.

Subsequently, an *Aspergillus niger* strain AB1.13 (Mattern, I. E. et al., 1992, Mol. Gen. Genet. 234:332-336) was co-transformed with the CAD expression vector and the MTT expression vector. AmdS transformants resulting for this experiment were purified by single colony purification and retested for their AmdS+ phenotype.

Analysis of *A. nicer* Transformants for Itaconic Acid Production

Several positive transformants and the parental host strain were subsequently cultured in Shake Flask in MM medium supplied with uridine containing glucose as C-source and nitrate as N-source. Medium samples from the various cultures were analyzed by HPLC for the presence of itaconic acid (Table 7).

Shake Flask Medium Compositions:

Per liter: 0.52 g of KCl, 2.4 g of NaNO$_3$, 1.56 g of KH$_2$PO$_4$, 0.24 g of MgSO$_4$*7H$_2$O, 5 mg of Fe(III)SO$_4$.7H$_2$O, 5 mg of MnCl$_2$*4H$_2$O, 0.022 g of ZnSO$_4$*7H$_2$O, 0.011 g of H$_3$BO$_3$, 1.7 mg of CoCl$_2$*6H$_2$O and 2.44 g of uridine, 100 g of glucose as a carbon source. All media were prepared in demineralised water.

(SEQ ID NOS: 10-11)

```
Translation of MTT cds (1-861)
Universal code
Total amino acid number: 286, MW = 31503
Max ORF starts at AA pos 1(may be DNA pos 1) for 286 AA(858 bases), MW = 31503
    1 ATGAGTATTCAACATTTCCGTGTCGCCCTTATTCCCTTTTTTGCGGCATTTTGCCTTCCT
    1 M  S  I  Q  H  F  R  V  A  L  I  P  F  F  A  A  F  C  L  P 61 GTTTTTGCTCACCCAGAAACGCTGGTGAAAGTAAAAGATGCTGAAGATCAGTTGGGTGCA
   21 V  F  A  H  P  E  T  L  V  K  V  K  D  A  E  D  Q  L  G  A 121 CGAGTGGGTTACATCGAACTGGATCTCAACAGCGGTAAGATCCTTGAGAGTTTTCGCCCC
   41 R  V  G  Y  I  E  L  D  L  N  S  G  K  I  L  E  S  F  R  P 181 GAAGAACGTTTTCCAATGATGAGCACTTTTAAAGTTCTGCTATGTGGCGCGGTATTATCC
   61 E  E  R  F  P  M  M  S  T  F  K  V  L  L  C  G  A  V  L  S 241 CGTATTGACGCCGGGCAAGAGCAACTCGGTCGCCGCATACACTATTCTCAGAATGACTTG
   81 R  I  D  A  G  Q  E  Q  L  G  R  R  I  H  Y  S  Q  N  D  L 301 GTTGAGTACTCACCAGTCACAGAAAAGCATCTTACGGATGGCATGACAGTAAGAGAATTA
  101 V  E  Y  S  P  V  T  E  K  H  L  T  D  G  M  T  V  R  E  L 361 TGCAGTGCTGCCATAACCATGAGTGATAACACTGCGGCCAACTTACTTCTGACAACGATC
  121 C  S  A  A  I  T  M  S  D  N  T  A  A  N  L  L  L  T  T  I 421 GGAGGACCGAAGGAGCTAACCGCTTTTTTGCACAACATGGGGGATCATGTAACTCGCCTT
  141 G  G  P  K  E  L  T  A  F  L  H  N  M  G  D  H  V  T  R  L 481 GATCGTTGGGAACCGGAGCTGAATGAAGCCATACCAAACGACGAGCGTGACACCACGATG
  161 D  R  W  E  P  E  L  N  E  A  I  P  N  D  E  R  D  T  T  M 541 CCTGTAGCAATGGCAACAACGTTGCGCAAACTATTAACTGGCGAACTACTTACTCTAGCT
  181 P  V  A  M  A  T  T  L  R  K  L  L  T  G  E  L  L  T  L  A 601 TCCCGGCAACAATTAATAGACTGGATGGAGGCGGATAAAGTTGCAGGACCACTTCTGCGC
  201 S  R  Q  Q  L  I  D  W  M  E  A  D  K  V  A  G  P  L  L  R 661 TCGGCCCTTCCGGCTGGCTGGTTTATTGCTGATAAATCTGGAGCCGGTGAGCGTGGGTCT
  221 S  A  L  P  A  G  W  F  I  A  D  K  S  G  A  G  E  R  G  S 721 CGCGGTATCATTGCAGCACTGGGGCCAGATGGTAAGCCCTCCCGTATCGTAGTTATCTAC
  241 R  G  I  I  A  A  L  G  P  D  G  K  P  S  R  I  V  V  I  Y 781 ACGACGGGGAGTCAGGCAACTATGGATGAACGAAATAGACAGATCGCTGAGATAGGTGCC
  261 T  T  G  S  Q  A  T  M  D  E  R  N  R  Q  I  A  E  I  G  A

841 TCACTGATTAAGCATTGGTAA
  281 S  L  I  K  H  W  *
```

HPLC analysis was performed with a reversed phase column, using a Develosil™ 3 µm RP-Aqueous C30 140A column at a constant temperature of 25° C., with elution with 20 mM NaH2PO4, pH 2.25 and acetonitril. Compounds were detected by UV at 210 nm using a Waters 2487 Dual wavelength Absorbance detector (Milford, Mass., USA). Retention time of itaconic acid was 18.82 min.

TABLE 7

Itaconic acid concentration in the culture fluid of the A. niger AB1.13 transformants cultivated in shake flasks. Aspergillus niger AB 1.13 transformants (AB 1.13 CAD)

| strain | code | time (hrs) | itaconic acid mg/g wet weight |
|---|---|---|---|
| AB 1.13 | WT | 54 | 0 |
| AB 1.13 CAD | 5.1 | 54 | 1.0 |
| AB 1.13 CAD | 7.2 | 54 | 0.7 |
| AB 1.13 CAD | 10.1 | 54 | 1.4 |
| AB 1.13 CAD | 14.2 | 54 | 1.2 |
| AB 1.13 CAD | 16.1 | 54 | 1.2 |
| AB 1.13CAD + MTT | 4.1 | 54 | 1.3 |

TABLE 7-continued

Itaconic acid concentration in the culture fluid of the A. niger AB1.13 transformants cultivated in shake flasks. Aspergillus niger AB 1.13 transformants (AB 1.13 CAD)

| strain | code | time (hrs) | itaconic acid mg/g wet weight |
|---|---|---|---|
| AB 1.13CAD + MTT | 6.2 | 54 | 1.5 |
| AB 1.13CAD + MTT | 2.2.1 | 54 | 2.2 |

No itaconic acid was detected in the supernatant of the parental strain while in the culture fluid of the strains containing the CAD gene (strains marked CAD), itaconic acid was detected (Table 7).

In both the culture fluid of the strains containing the CAD gene and the strains containing both the CAD gene and MTT gene (strains marked CAD+MTT), itaconic acid was detected. In at least 2 of the MTT expressing strains more itaconic acid was produced in the culture fluid than in the strains expressing only the CAD gene. Moreover, the average itaconic acid concentration was higher in the culture fluid of the strains expressing both the CAD and the MTT gene than in the strains expressing the CAD gene only (1.7 versus 1.1 mg itaconic acid/g mycelial wet weight).

The invention claimed is:

1. A host cell which has been modified to contain a heterologous gene encoding a protein that transports di/tricarboxylate from the mitochondrion to the cytosol, wherein said protein has an amino acid sequence at least 95% identical to ATEG_09970.1 of SEQ ID NO:3.

2. The host cell of claim 1, wherein said protein is a tricarboxylate transporter.

3. The host cell of claim 1, wherein said protein transports cis-aconitate, citrate or isocitrate.

4. The host cell of claim 1, wherein said host cell is from of a citrate producing microorganism.

5. The host cell of claim 1, wherein said gene comprises
1) a nucleic acid sequence encoding a mitochondrial tricarboxylic acid transporter from *A. terreus, A. niger, A. itaconicus, A. nidulans, A. oryzae,* or *A. fumigates,* or 2) a nucleic acid sequence which encodes the amino acid sequence of ATEG_09970.1 of SEQ ID NO:3.

6. The host cell of claim 1, wherein a nucleic acid encoding the enzyme cis-aconitic acid decarboxylase (CAD) and/or a nucleic acid encoding a Major Facilitator Superfamily (MFS) transporter is co-introduced.

7. The host cell of claim 4, wherein the citrate producing micro-organism is *A. terreus, A. niger, A. itaconicus, A. nidulans, A. oryzae, A. fumigates, Yarrowia lipolytica, Ustilago zeae, Candida* sp., *Rhodotorula* sp., *Pseudozyma antarctica, E. coli,* or *Saccharomyces cerevisiae.*

8. The host cell of claim 1, which is of a lovastatin producing microorganism.

9. The host cell of claim 6, wherein the CAD is encoded by the nucleotide sequence comprised in ATEG_09971.1 (SEQ ID NO:5).

10. The host cell of claim 6, wherein the MFS transporter is encoded by the nucleotide sequence comprised in ATEG_09972.1 (SEQ ID NO:13).

11. The host cell of claim 8, wherein the lovastatin producing micro-organism is from *Monascus* spp., *Penicillium* spp., *Hypomyces* spp., *Doratomyces* spp., *Phoma* spp., *Eupenicillium* spp., *Gymnoascus* spp., *Pichia labacensis, Candida cariosilognicola, Paecilomyces varioti, Scopulariopsis brevicaulis* or *Trichoderma* spp.

12. The host cell of claim 7, which is of *A. terreus* or *A. niger.*

13. The host cell of claim 1, wherein the encoding nucleotide sequence is expressed from a vector comprising a promoter capable of driving expression of said sequence.

* * * * *